(12) United States Patent
Byland et al.

(10) Patent No.: US 7,988,660 B2
(45) Date of Patent: Aug. 2, 2011

(54) NEEDLE-FREE INJECTION DEVICE

(75) Inventors: Timothy D. Byland, Maple Grove, MN (US); James Matthew Collins, Arlington, MA (US); Mark James Fisher, Highland Park, IL (US); John Grimley, Kenosha, WI (US); Mehran Mojarrad, Westfield, IN (US); John Michael O'Fallon, Lowell, MA (US); Craig Field Sampson, Lake Bluff, IL (US); James G. Tappel, Cincinnati, OH (US)

(73) Assignee: Eli Lilly and Company, Indianapolis, IN (US)

( * ) Notice: Subject to any disclaimer, the term of this patent is extended or adjusted under 35 U.S.C. 154(b) by 128 days.

(21) Appl. No.: 12/091,176

(22) PCT Filed: Dec. 19, 2006

(86) PCT No.: PCT/US2006/048422
§ 371 (c)(1),
(2), (4) Date: Apr. 23, 2008

(87) PCT Pub. No.: WO2007/075677
PCT Pub. Date: Jul. 5, 2007

(65) Prior Publication Data
US 2008/0319383 A1   Dec. 25, 2008

Related U.S. Application Data

(60) Provisional application No. 60/752,063, filed on Dec. 20, 2005.

(51) Int. Cl.
*A61M 5/30* (2006.01)

(52) U.S. Cl. ........................................................ 604/70
(58) Field of Classification Search ...................... None
See application file for complete search history.

(56) References Cited

U.S. PATENT DOCUMENTS 3,202,151 A   8/1965  Kath
(Continued)

FOREIGN PATENT DOCUMENTS
EP          1277487 A1   1/2003
(Continued)

OTHER PUBLICATIONS

The International Bureau of WIPO, International Preliminary Report on Patentability in PCT Application No. PCT/US2006/048422, Nov. 27, 2008.

(Continued)

*Primary Examiner* — Nicholas D Lucchesi
*Assistant Examiner* — Pritesh Patel
(74) *Attorney, Agent, or Firm* — Wood, Herron & Evans, LLP

(57) ABSTRACT

A fluid injecting device (30) generally including a fluid delivery assembly (32) and a needle-free injecting assembly (34). The fluid delivery assembly (32) delivers or transfers the fluid medicine from a cartridge (40) into the needle-free injecting assembly (34) for injecting into a patient. A drive train (112) applies a force to a piston (64) inside the cartridge (40) during the delivery of the fluid to the needle-free injecting assembly (34) to prevent adhesion or static friction between the piston (64) and the cartridge (40). In addition, sensors can be used to help ensure the proper amount of dosage is transferred to the needle-free injecting assembly, conserve power, reduce leakage during disassembly, among other functions.

24 Claims, 12 Drawing Sheets

U.S. PATENT DOCUMENTS

| | | | |
|---|---|---|---|
| 4,338,980 | A | 7/1982 | Schwebel et al. |
| 4,560,377 | A | 12/1985 | Geat et al. |
| 4,623,332 | A | 11/1986 | Lindmayer et al. |
| 4,856,567 | A | 8/1989 | Cosmai |
| 4,877,065 | A | 10/1989 | Lamboy et al. |
| 5,503,628 | A | 4/1996 | Fetters et al. |
| 5,505,697 | A | 4/1996 | McKinnon, Jr. et al. |
| 5,546,996 | A | 8/1996 | Broyles et al. |
| 5,746,714 | A | 5/1998 | Salo et al. |
| 5,846,233 | A | 12/1998 | Lilley et al. |
| 5,954,689 | A | 9/1999 | Poulsen |
| 5,993,412 | A * | 11/1999 | Deily et al. ............... 604/68 |
| 6,056,716 | A | 5/2000 | D'Antonio et al. |
| 6,165,155 | A | 12/2000 | Jacobsen et al. |
| 6,171,276 | B1 * | 1/2001 | Lippe et al. ............... 604/67 |
| 6,174,304 | B1 | 1/2001 | Weston |
| 6,251,091 | B1 | 6/2001 | Weston |
| 6,270,473 | B1 | 8/2001 | Schwebel |
| 6,277,091 | B1 | 8/2001 | Genet |
| 6,302,160 | B2 | 10/2001 | Castellano |
| 6,340,357 | B1 | 1/2002 | Poulsen et al. |
| 6,364,865 | B1 | 4/2002 | Lavi et al. |
| 6,425,879 | B1 | 7/2002 | Egger et al. |
| 6,508,788 | B2 | 1/2003 | Preuthun |
| 6,552,483 | B1 | 4/2003 | Cho et al. |
| 6,610,042 | B2 | 8/2003 | Leon et al. |
| 6,652,483 | B2 | 11/2003 | Slate et al. |
| 6,669,664 | B2 | 12/2003 | Slate et al. |
| 6,673,035 | B1 | 1/2004 | Rice et al. |
| 6,689,101 | B2 * | 2/2004 | Hjertman et al. ............... 604/131 |
| 6,893,415 | B2 | 5/2005 | Madsen et al. |
| 2002/0055707 | A1 * | 5/2002 | Slate et al. ............... 604/72 |
| 2003/0139707 | A1 | 7/2003 | Hommann et al. |
| 2004/0059286 | A1 | 3/2004 | Slate et al. |

FOREIGN PATENT DOCUMENTS

| | | |
|---|---|---|
| JP | 2004321579 A | 11/2004 |
| WO | 01/30425 A1 | 5/2001 |
| WO | 02/087663 A2 | 11/2002 |
| WO | 02/102295 A2 | 12/2002 |

OTHER PUBLICATIONS

U.S. Patent and Trademark Office, International Search Report and Written Opinion in PCT Application Serial No. PCT/US2006-048422, Oct. 2008.

* cited by examiner

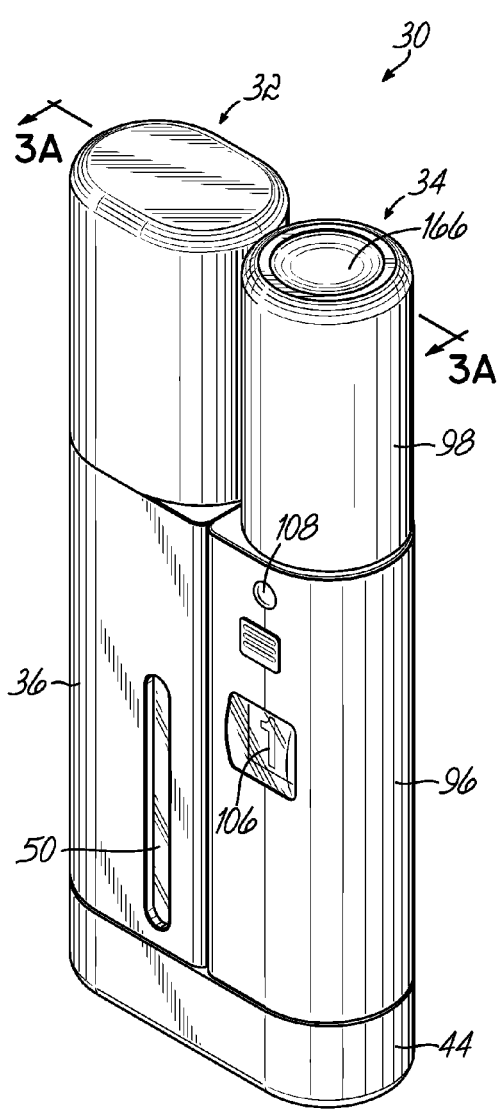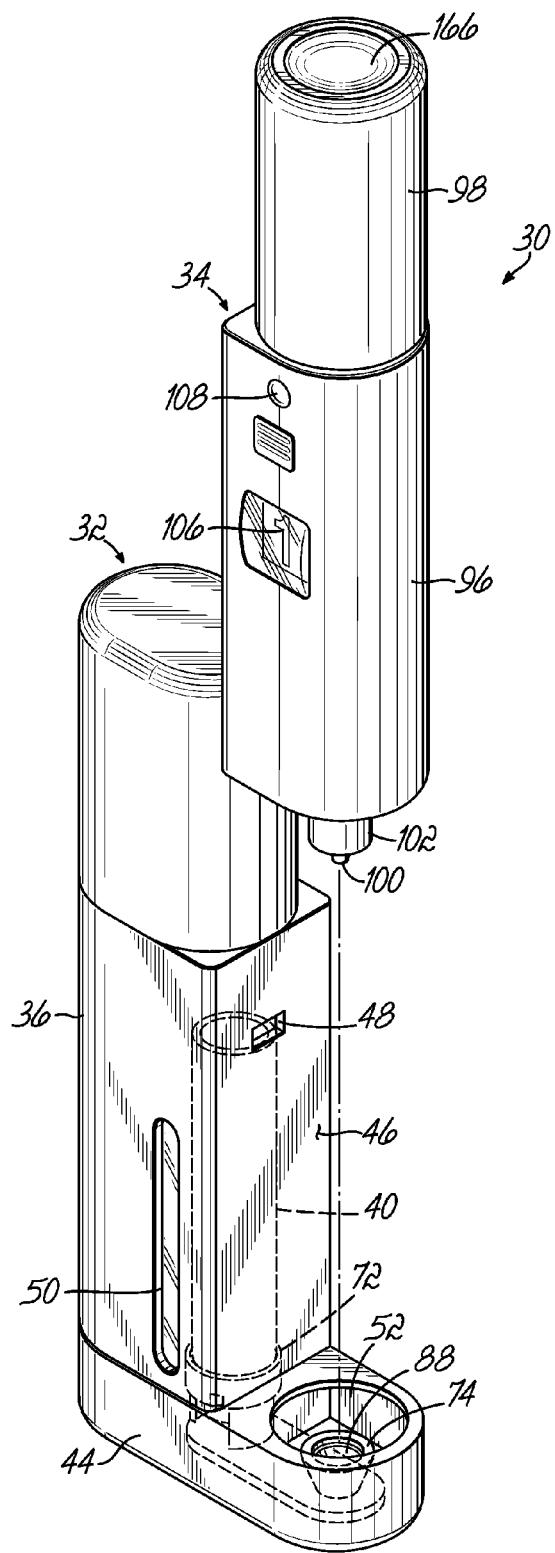
FIG. 1
FIG. 1A

NEEDLE-FREE INJECTION DEVICE

This application claims the benefit of U.S. Provisional Application Ser. No. 60/752,063 filed on Dec. 20, 2005, the disclosure of which is hereby incorporated by reference herein.

TECHNICAL FIELD OF THE INVENTION

The present invention relates to needle-free injectors for delivering medicated fluid into a body of a patient.

BACKGROUND

Using a needle-free injection device to inject medicated fluid into the body is well known in the art. For instance, U.S. Pat. No. 6,673,035 discloses a needle-free injector that administers medication as a fine, high velocity jet. This high velocity jet is delivered to the injection site under sufficient pressure to enable the liquid jet to pass through the skin without having to puncture the skin.

U.S. Pat. No. 6,673,035 discloses a device that includes two main sections. The first section contains a disposable cartridge that carries the fluid medication that will be injected into the body. The second section is a needle-free injecting assembly that is designed to pressure inject the fluid into the body at a specified location.

Using the needle-free injector of U.S. Pat. No. 6,673,035 enables medication to be administered without all of the problems associated with using a traditional syringe and needle puncturing the skin. Limitations on the device disclosed in U.S. Pat. No. 6,673,035, however, exist. For instance, the two main sections of the device are placed co-linear. Therefore, the device can be difficult to use, especially by a patient lacking dexterity, because it occupies a great deal of space in one direction. Another challenge with the device is the cartridge includes a movable piston that should change position inside of the cartridge as fluid is withdrawn from the cartridge. Such pistons can, however, fail to move in various situations because of adhesion or static friction between the piston and the cartridge wall. U.S. Pat. No. 6,673,035 does disclose initially displacing the movable piston during installation of the cartridge, however, adhesion or static friction between the piston and the cartridge wall can still be a problem especially during subsequent times of use.

In addition, fluid leakage and power conservation can be problems with prior needle-free injectors.

SUMMARY

In one embodiment of the invention, the device includes a needle-free injecting assembly for injecting a fluid dose into a body. The device also includes a fluid delivery assembly coupled to the needle-free injecting assembly. The fluid delivery assembly is configured to deliver the fluid dose to the needle-free injecting assembly and includes a cartridge for storing the fluid dose. The fluid delivery assembly has a movable piston contained inside the cartridge. The fluid delivery assembly also includes a drive train for applying a force to the moveable piston. The force applied to the moveable piston is at least initially sufficient to overcome the static friction between the cartridge and the moveable piston.

In another aspect, the device includes a needle-free injecting assembly for injecting the fluid dose into a body generally along a first axis. The device also includes a fluid delivery assembly coupled to the needle-free injecting assembly. The fluid delivery assembly is configured to deliver fluid to the needle-free injecting assembly and includes a cartridge for storing the fluid dose. The fluid delivery assembly is positioned in a side-by-side arrangement to the needle-free injecting assembly. The device also includes a fluid flow passage extending transverse to the first axis and communicating between the cartridge and the needle-free injecting assembly.

A further aspect to the invention is a medication refill unit for insertion into a device for injecting a fluid into a body. A medication refill unit includes a cartridge containing the fluid. The medication refill unit also includes an adapter having a first fluid passage fluidly coupled to the cartridge, a second fluid passage adapted to be fluidly coupled to the needle-free injecting assembly, and a third fluid passage in fluid communication between the first fluid passage and the second fluid passage. The third fluid passage extends transverse to the first and second fluid passages.

In another aspect of the invention, the device includes a needle-free injecting assembly and a fluid delivery assembly configured to deliver the fluid dose into the needle-free injecting assembly. The fluid delivery assembly includes a housing defining an interior space therein. The fluid delivery assembly also includes a cartridge defining a reservoir for containing the fluid. The cartridge is constructed and arranged to be received by the interior space. The cartridge has a first end and a second end defining an outlet. A movable piston is accessible through the first end of the cartridge. The fluid delivery assembly further includes a drive train for applying a force to the movable piston and a sensing assembly constructed and arranged to control at least the drive train. The device also includes an adapter removably coupled to the needle-free injecting assembly and fluidly coupling the cartridge to the needle-free injecting assembly. The adapter has a fluid flow passage extending transverse to an axis extending along a length of the needle-free injecting assembly. The sensing assembly directs the drive train to apply a force to the movable piston for preventing adhesion or static friction between the movable piston and the interior surface of the cartridge during delivery of the fluid from the cartridge to the needle-free injecting assembly.

A further aspect of the invention contemplates a method for ensuring a sufficient dose of fluid exists inside a cartridge used with an electronically controlled pressure injection device. The method includes checking the level of fluid in the cartridge at least periodically using a sensing assembly of the device and also includes determining if the cartridge contains sufficient fluid for a specified dose using the sensing assembly of the device. The method also includes electronically indicating if the dose is insufficient.

Another method of the invention includes altering the dose of a fluid prior to injection. The method includes inserting a cartridge containing the fluid into a fluid delivery assembly. The method also includes transferring the fluid from a fluid delivery assembly to a needle-free injecting assembly with the assistance of a drive train. The drive train can move in different directions to assist in altering the amount of fluid being transferred between the fluid delivery assembly and the needle-free injecting assembly.

An additional aspect of the invention includes a method of delivering a fluid from a cartridge of a fluid delivery assembly into a needle-free injecting assembly syringe that is in fluid communication with the cartridge. The method includes negatively pressurizing the needle-free syringe by inducing a vacuum to transfer the fluid into the needle-free syringe from the cartridge. The method also includes at least initially assisting the transfer of the fluid by using a drive train to apply a force to a piston in the cartridge.

A further aspect is a method for preventing leaking of fluid between a needle-free injecting assembly and a fluid delivery assembly in a fluid delivery device. The method includes sensing the removal of the needle-free injecting assembly from the fluid delivery assembly. In addition, the method also includes depressurizing the fluid in the fluid delivery assembly in response to initiating the removal of the needle-free injecting assembly.

An additional aspect is a method for conserving power in a needle-free fluid delivery device. The method includes sensing if the needle-free fluid delivery device has been operated over a predetermined time period and entering a sleep mode in response to the lack of operation over the predetermined time period.

Another aspect of the invention is a needle-free device for injecting a fluid dose into a body of a patient. The needle-free device includes an injecting assembly constructed and arranged to deliver the fluid dose into the body. The needle-free device also includes a fluid delivery assembly configured to deliver the fluid dose to the injecting assembly. The fluid delivery assembly includes a cartridge defining a reservoir for containing the fluid. The cartridge has a first end and a second end defining an outlet. The fluid delivery assembly also includes a movable piston within the first end of the cartridge. Furthermore, the fluid delivery assembly includes an adapter removably coupled to the injecting assembly and fluidly coupling the cartridge to the injecting assembly, and a powered drive train for applying a force to the movable piston for facilitating aspiration of the fluid from the cartridge to the coupled injecting assembly.

A further aspect of the invention includes a needle-free device for injecting a fluid dose into a body of a patient. The needle-free device includes an injecting assembly constructed and arranged to deliver the fluid dose into the body. The needle-free device also includes a fluid delivery assembly configured to deliver the fluid dose to the injecting assembly. The fluid delivery assembly includes a cartridge defining a reservoir for containing the fluid and having a first end and a second end defining an outlet. The fluid delivery assembly also includes a movable piston contained within the first end of the cartridge and an adapter removably coupled to the injecting assembly. The adapter fluidly couples the cartridge to the injecting assembly. The fluid delivery assembly also includes a powered drive train for applying a force to the movable piston and a sensing assembly constructed and arranged to sense the force applied to the movable piston. The sensing assembly also controls at least the drive train to direct the drive train to apply the force to the movable piston for preventing the adhesion or static friction during delivery of the fluid from the cartridge to the injecting assembly.

Various additional advantages, features and objectives of the invention will become apparent upon review of the following detailed description of an illustrative embodiment shown and described in connection with the accompanying drawings.

BRIEF DESCRIPTION OF DRAWINGS

FIG. 1 illustrates a perspective view of an assembled fluid injection device according to one illustrative embodiment.

FIG. 1A illustrates a perspective view of the fluid injection device of FIG. 1 having the needle-free injecting assembly removed from the fluid delivery assembly and further showing the cartridge and adapter in dashed or phantom lines.

DETAILED DESCRIPTION OF THE ILLUSTRATIVE EMBODIMENTS

Figure 2:
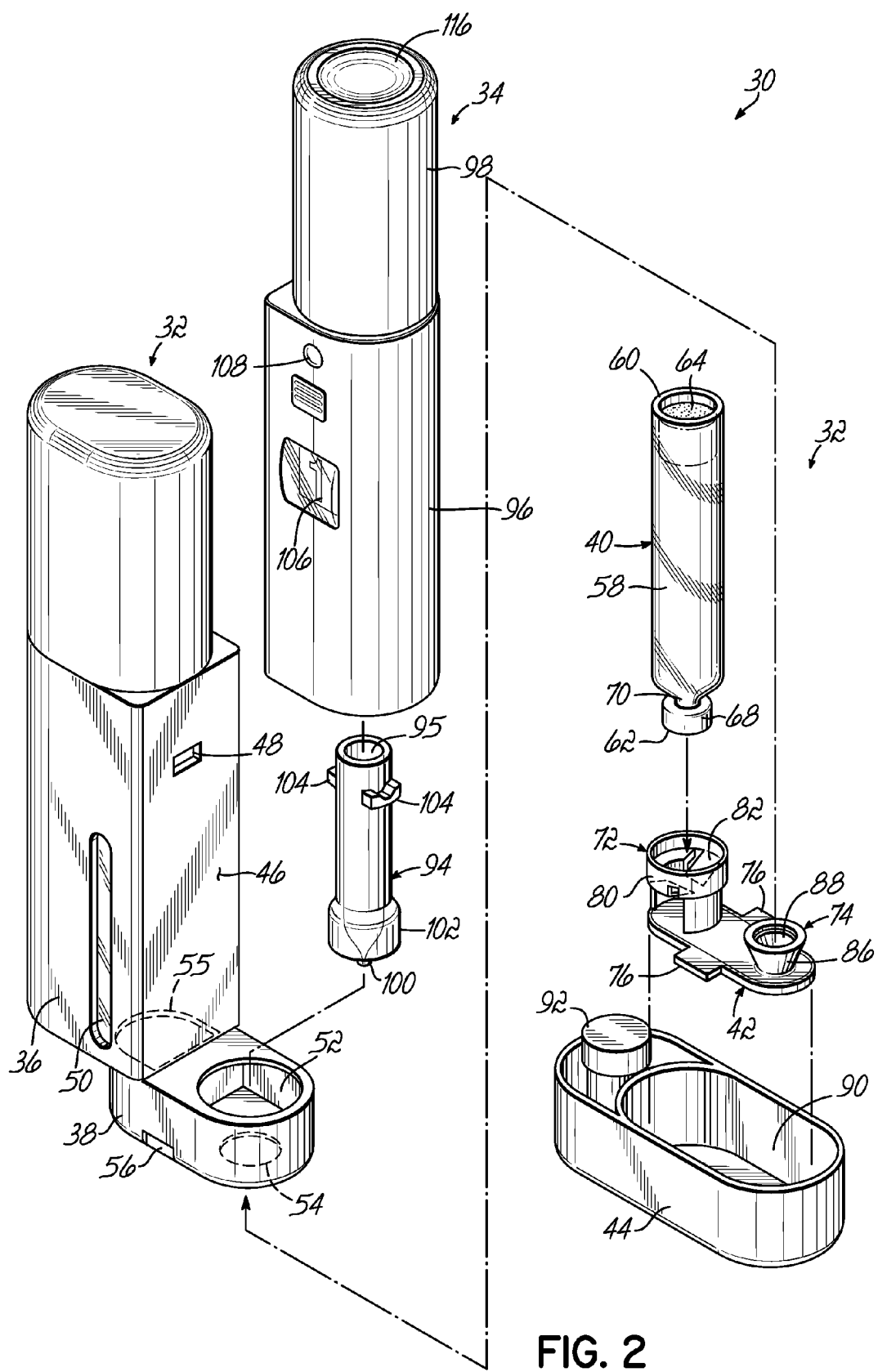
FIG. 2 illustrates an exploded view of the fluid injection device of FIG. 1.

Referring now to the drawings, FIG. 1 illustrates a fluid injection device 30. The fluid injection device 30 is separated into a fluid delivery assembly 32 and a needle-free injecting assembly 34. The fluid delivery assembly 32 includes a variety of components that cooperate together to store and transfer the fluid medicine into the needle-free injecting assembly 34. The needle-free injecting assembly 34 also contains a variety of components that cooperate together to draw a dose of fluid medicine out of the fluid delivery assembly 32 and inject the fluid medicine into the body. FIG. 1 illustrates that the needle-free injecting assembly 34 is positioned in a side-by-side arrangement with the fluid delivery assembly 32. This arrangement makes the fluid injection device 30 easier to use and store.

Referring to FIG. 1A, the needle-free injecting assembly 34 is illustrated removed from the fluid delivery assembly 32. The needle-free injecting assembly 34 can be removed after the needle-free injecting assembly 34 has obtained a desired fluid dose. The needle-free injecting assembly 34 can then be pressed against the body to inject the fluid dose obtained. FIG. 1A illustrates other components of the fluid delivery assembly 32 in shadow. These components are described in more detail hereinbelow with respect to FIG. 2.

FIG. 2 illustrates how some of the different components of the fluid injection device 30 cooperate inside both the fluid delivery assembly 32 and needle-free injecting assembly 34. In the illustrated embodiment, the fluid delivery assembly 32 has five major illustrated components. The components are a housing 36 for providing structure and an interior area to hold other components, a base portion 38 for combining other components together, a cartridge 40 for containing the fluid medicine, an adapter 42 for fluidly coupling the fluid delivery assembly 32 to the needle-free injecting assembly 34, and an end cap 44 for securing the assembled components to the housing 36. Other components of the fluid delivery assembly 32 exist and are discussed hereinbelow in more detail with respect to FIGS. 3A-3D. Those of ordinary skill in the art recognize that the components can be altered or combined in different ways in different embodiments.

The housing 36 provides structure to the fluid delivery assembly 32. In some embodiments, the housing 36 is formed of two or more pieces that combine together to facilitate manufacturing the housing 36. The housing 36 includes an outer surface 46 that can be constructed of metal or a high strength plastic. The outer surface 46 defines an interior area inside of the housing 36 designed to receive a power source 110 (FIGS. 3A and 3B), such as a battery, and the cartridge 40. In addition, in other embodiments the outer surface 46 defines a window 108 that enables a signal light 108a (see FIG. 4) to shine through. The signal light can indicate that the dose is insufficient, that a battery is running out of power that injecting assembly 34 is coupled to fluid delivery assembly 32, that device 30 is ready for injecting assembly 34 to be removed, or even a display unit can be provided to provide in-depth information. In some other embodiments, the dose sufficiency can be indicated by activating an acoustical indicator. Moreover, the location of this signal light or display unit can vary in different embodiments depending upon the available space and user preferences. In the illustrated embodiment, the housing 36 also includes the latch depression 48 that is configured to enable a mechanical latching device 97, 132 (FIGS. 3A and 3B) to couple the fluid delivery assembly 32 to the needle-free injecting assembly 34. The mechanical latching device is described in further detail hereinbelow with respect to FIG. 4. Other embodiments use a magnet to couple the fluid delivery assembly 32 to the needle-free injecting assembly 34. The housing 36 also includes a window 50 that is aligned with the area that receives the cartridge 40. Accordingly, the window 50 enables a user to visually determine how much fluid medicine is left in the cartridge 40.

The fluid delivery assembly 32 also includes the base portion 38. The base portion 38 is simply an extension of the housing 36 and therefore is rigidly coupled to the housing 36. The base portion 38 defines a first aperture 52 that enables the needle-free injecting assembly 34 to be received by the fluid delivery assembly 32 and a second aperture 54 for allowing the adapter 42 to be received. The first and second apertures 52, 54 are positioned co-linear to enable the adapter 42 to come into contact with the needle-free injecting assembly 34 for assisting the transfer of fluid medicine from the fluid delivery assembly 32 to the needle-free injecting assembly 34. In addition, an empty space is positioned between the first and second apertures 52, 54 to help facilitate this combination. The base portion 38 also includes indentations 56 that correspond to the adapter 42 for facilitating the insertion and removal of the adapter 42 into the base portion 38.

Another component of the fluid delivery assembly 32 is the cartridge 40. The cartridge 40 contains the fluid medicine. In some embodiments, the medicine is insulin; in other embodiments the medicine can be a pain medication, steroid, hormones, antibiotics, or any other type of medicine. The cartridge 40 includes a cartridge body 58 that is generally cylindrical that defines an open area in the interior for holding the fluid. The cartridge body 58 is usually formed of glass or a plastic, however, the construction of the cartridge body 58 is not limited to these materials. In many embodiments, the cartridge body 58 is made of a translucent material to enable the user to observe the amount of fluid medicine that remains through the window 50. The cartridge 40 also includes a first end 60 that is an open end and a second end 62 that is a closed end.

The first end 60 is open and generally cylindrical and receives a movable piston 64. The movable piston 64 is designed to snugly fit inside of the cartridge body 58. In the illustrated embodiment, the movable piston 64 is composed of a plastic or rubber material in the shape of a cylinder having circumferential grooves around its outer surface. Those skilled in the art recognize the movable piston 64 can possess other shapes, materials, groove patterns, or other features in other embodiments. In the illustrated embodiment, the movable piston 64 provides an airtight seal to contain the fluid medicine.

The second end 62 is closed through the use of an elastomeric septum 66 that is held in place by a metal cap 68. The metal cap 68 and the elastomeric septum 66 are placed on the tapered neck portion 70 of the cartridge body 58. This neck portion 70 ends in an opening that would allow fluid medicine to flow out of the cartridge 40 if the elastomeric septum 66 were not present. In addition, the metal cap 68 is sized to cooperate with the adapter 42 to lockingly engage the cartridge 40 to the adapter 42 after the adapter 42 has been inserted.

The adapter 42 is the component of the fluid delivery assembly 32 that fluidly couples the other components of the fluid delivery assembly 32 to the needle-free injecting assembly 34. In most embodiments, the adapter 42 is constructed by ultrasonically welding together two pieces of injection-molded polymers. The adapter 42 includes a receiving structure 72 for receiving the cartridge 40 and a cup 74 for receiving the needle-free injecting assembly 34. The receiving structure 72 and the cup 74 are spaced laterally from each other to conform to the side-by-side arrangement of the fluid delivery assembly 32 and the needle-free injecting assembly 34. The adapter 42 also includes flaps 76 that are designed to cooperate with the indentations 56 of the base portion 38 to facilitate easy insertion and removal of the adapter 42 from the base portion 38. The flaps 76 of the illustrated embodiment are rectangular shaped, however, in other embodiments the flaps 76 can define other shapes.

The receiving structure 72 is configured to receive the cartridge 40. The receiving structure 72 includes a supporting structure 78 for supporting the remainder of the receiving structure 72, a collar 80 that surrounds the outer periphery of the cartridge 40 when the cartridge is inserted, a set of flanges 82 that lockingly engage the metal cap 68 of the cartridge 40 when inserted, and a hollow piercing member 84 that penetrates through the elastomeric septum 66 when the cartridge 40 is inserted into the receiving structure 72. The supporting structure 78 has a diameter that is smaller than the diameter of the collar 80 and is open in some portions allowing visual inspection of the insertion of the cartridge 40. The collar 80 has a diameter that is slightly larger than the diameter of the cartridge body 58 to snugly restrain the cartridge body 58 around its periphery. In some embodiments, the collar 80 is approximately one centimeter above the base of the adapter 42. The collar 80 includes sections that align with the open portions of the supporting structure 78 that are narrower to allow the proper angling of the flanges 82. In the illustrated embodiment, the flanges 82 are resilient and generally rectangular. Other shapes can be used in other embodiments. The flanges 82 are biased towards the center of the receiving structure 72. During insertion of the cartridge 40, the size of the metal cap 68 forces the flanges 82 away from the center of the receiving structure 72. Once the metal cap 68 has passed by the flanges 82, the flanges 82 resiliently spring back towards the center of the receiving structure 72 and come to rest around the neck portion 70. At this point, the flanges 82 touch the top of the metal cap 68. The flanges 82 therefore maintain the cartridge 40 and adapter 42 in a fixed axial relationship with each other. If an attempt to remove the cartridge 40 were made, the flanges 82 would apply an opposing force to the top of the metal cap 68. The cartridge 40 could only be removed if flanges 82 were broken off or rendered inoperable. The design encourages the use of a new adapter 42 every time a new cartridge 40 is needed.

The receiving structure 72 also includes a piercing member 84 for entering a hole in the metal cap 68 and piercing the elastomeric septum 66 of the cartridge 40. The piercing member 84 is hollow and includes a first fluid passage 140 (see FIGS. 3A and 3B) that assists with delivering the fluid from the cartridge 40 into the needle-free injecting assembly 34. The piercing member 84 can be formed of a metal, plastic, or other material so long as it is sufficiently rigid to pierce the elastomeric septum 66. The adapter 42 and cartridge 40 can be sold as a separate medication refill unit. The adapter 42 and cartridge 40 can be sold as kit that requires assembling the components together after purchase. In addition, the adapter 42 and cartridge 40 can be sold pre-assembled with the cartridge 40 inserted into the receiving structure 72 and the piercing member 84 having already pierced the elastomeric seal 66. The pre-assembled medication refill unit would preferably prevent the re-use of the adapter 42 with different cartridges other than cartridge 40.

The adapter 42 also includes a cup 74. The cup 74 is constructed and arranged to receive the needle-free injecting assembly 34. The cup 74 includes an outer portion 86 that is rigid and an inner seal 88 that is compliant. In the illustrated embodiment, the outer portion 86 is injection molded like the rest of the components of the adapter 42 and is formed from the same polymer. The outer portion 86 therefore is rigid and concave and designed to contain the inner seal 88. The outer portion 86 has an opening in the bottom of the concave recess that connects to a fluid passageway 142. The fluid passageways that enable fluid communication between the cartridge 40 and the needle-free injecting assembly 34 are illustrated and described in more detail hereinbelow with respect to FIGS. 3A-D. In addition, the outer portion 86 includes ridges or other texturing configurations on the interior concave surface that increase the friction and surface area that will be exposed to the inner seal 88 to help attach the inner seal 88 to the outer portion 86. The inner seal 88 is usually an elastomeric seal, such as polycarbonate or silicone rubber; however, in some embodiments a different material is used. The inner seal 88 contains an opening or a zero diameter hole, such as a slit, that allows fluid communication through the inner seal 88 to the fluid passageway 144 present in the bottom of the concave recess of the outer portion 86. The inner seal 88 assists in ensuring an airtight seal between the adapter 42 and the needle-free injecting assembly 34.

The fluid delivery assembly 32 also includes the end cap 44. The end cap 44 assists with containing all of the other components of the fluid delivery assembly 32 and the needle-free injecting assembly 34 in a side-by-side relationship. The end cap 44 is usually formed of a plastic or metal material, however, those skilled in the art recognize other materials are available, such as a ceramic. The end cap 44 includes a recess 90 that is constructed to receive the base portion 38, the adapter 42, and the cartridge 40 in combination after the adapter 42 has been inserted into the base portion 38. The end cap 44 also includes a post 92 constructed of a metal cap that sits on top of a plastic rod. The post 92 is designed to contact a negative pole of a power source 110. The post 92 provides the dual function of holding the power source 110 inside of the housing 36 and providing a metal contact to allow the completion of the circuit. Other embodiments can fail to include a post 92, as the power source can be located in other positions.

The needle-free injecting assembly 34, as illustrated, includes three main components. Other components exist that are described in more detail hereinbelow with respect to FIGS. 3A-D. The needle-free injecting assembly 34 includes a disposable needle-free syringe 94 for containing the fluid medicine in an interior space 95 or reservoir once it has been withdrawn from the fluid delivery assembly 32, an injection housing 96 for providing structure and containing the various internal components of the needle-free injecting assembly 34, and a winding sleeve 98 that triggers the withdrawal of fluid medicine in a predetermined amount based upon the amount of rotation of the winding sleeve 98. As known in the art, the needle-free syringe should be manufactured in accordance with accepted industry standards.

The needle-free syringe 94 includes a tapered end 100 that is received by the cup 74 of the adapter 42 and a hood 102 that covers the tapered end 100. The tapered end 100 includes a small opening at the end. In the illustrated embodiment, the opening is about 0.007 inches having a tolerance of no more than ±0.0005 inches. The small opening is critical in creating a high velocity fluid medicine jet that can penetrate into the body. The tapered end 100 is tapered so that the inner seal 88 of the cup 74 can surround the tapered end 100 and form an airtight seal. The hood 102 surrounds the upper portion of the cup 74 when the tapered end 100 is received to assist in preventing any spilling or spraying of fluid medicine due to a poor seal between the inner seal 88 and the tapered end 100. The needle-free syringe 94 also includes flanges 104 opposite to the tapered end 100 that cooperate with components of the needle-free injecting assembly 34 to hold and lock the needle-free syringe 94 in place during assembly and injection. These components will be discussed in greater detail with respect to FIGS. 3A-D.

The needle-free injecting assembly 34 also includes an injection housing 96. The injection housing 96 of the illustrated embodiment is formed from the same material as the housing 36 of the fluid delivery assembly 32. The injection housing 96 defines an interior space that receives the needle-free syringe 94 and the other components of the needle-free injecting assembly 34. The injection housing 96 also includes a catch 97 that cooperates with the latch depression 48 of the housing 36 to couple the injection assembly 34 to the fluid delivery assembly 32. The injection housing 96 also includes a dosage window 106 for indicating the amount of fluid dose that has been withdrawn and an indicator light 108 that indicates a condition of the needle-free injecting assembly 34. The dosage window 106 of the illustrated embodiment indicates a "1" which means one international unit of fluid medicine equivalent to 10 μl volume. The unit dose could vary from large to very small depending on the needs of the patient and the overall capacity of the needle-free injecting assembly 34. In other embodiments, the dosage window 106 could have a display that shows the amount of fluid dose in any desired units. The indicator light 108 indicates a condition of the needle-free injecting assembly 34, such as whether the needle-free injecting assembly 34 is properly coupled to the fluid delivery assembly 32. For instance, in one embodiment, the indicator light 108 can indicate a condition that the fluid in the system is currently pressurized by the force applied to movable piston 64 or by returning fluid back into the cartridge 40. Thus, the user can be informed when the needle-free injecting assembly 34 has been sufficiently depressurized and ready to be removed. Other types of conditions could be indicated by the indicator light 108, such as an insufficient dose in the needle-free injecting assembly 34, a failure of one of the internal components, fluid medicine remaining to be transferred into an initial partial dose the needle-free syringe 94 after injection, or any other desired information regarding status of the device 30. Any other type of display device may be used alternatively or in addition to provide any type of status information for device 30.

The needle-free injecting assembly 34 also includes the winding sleeve 98 that is located proximate to the injection housing 96. The winding sleeve 98 is the mechanism that the user uses to measure and set the amount of fluid medicine to be applied to the body. For example, suppose one 60° rotation of the winding sleeve 98 results in one unit of fluid medicine. If the user were to need four units of fluid medicine, the user would have to rotate the winding sleeve 98 240°. The winding sleeve 98 is usually formed of a plastic material, but in other embodiments other materials are used. The winding sleeve 98 is designed to be ergonomically compatible with the hand of an adult user to enable easy rotation of the winding sleeve 98. The winding sleeve 98 can rotate clockwise and counter-clockwise so that the dose can adjust to be larger or smaller. The rotation of winding sleeve 98 also serves as a signal to the electronic controller 116 that the system needs to make up and pressurize the cartridge 40 if the device 30 has been unattended for a set period of time causing the system to go into sleep mode. The sensor 134 is the transducer that detects movement of winding sleeve 98 and then communicates with the controller 116.

The different components of the fluid delivery assembly 32 and the needle-free injecting assembly 34 illustrated in FIG. 2 are assembled as follows. Initially, the cartridge 40 is inserted into the housing 36 of the fluid delivery assembly 32. Then, the receiving structure 72 of the adapter 42 is pressed onto the cartridge 40 to be fitted in base portion 38. Alternatively, adapter 42 may come pre-assembled and packaged with the cartridge 40 in a sterile medication refill unit. Assembling the cartridge 40 with the receiving structure 72 causes the piercing member 84 to penetrate into the elastomeric septum 66 of the cartridge 40. In addition, the cartridge 40 is axially fixed to the adapter 42 because of the flanges 82. The piercing member 84 provides fluid communication between the cartridge 40 and the adapter 42.

The medication refill unit formed of the combination of the adapter 42 and the cartridge 40 is then inserted into the base portion 38 and the housing 36. The cartridge 40 has the majority of the cartridge body 58 received inside the housing 36. This portion of the cartridge body 58 is observable through the window 50 of the housing 36. The other portion of the cartridge 40 having the second end 62 is received inside the base portion 38. The adapter 42 is received by the base portion 38 with the cup 74 passing through the second aperture 54 into the open area between the first and second apertures 52, 54. The receiving structure 72 passes through another opening 55 in the base portion 38 and is located inside another open area in the base portion 38. The flaps 76 of the adapter 42 are received by the indentations 56 of the base portion 38 to enable easy removal of the adapter 42. After the combination of the cartridge 40 and the adapter 42 has been inserted, the end cap 44 covers the base portion 38. The power source 110 needs to be inserted into the housing 36 before the end cap 44 is placed over the base portion 38. The frequency of changing the power source is independent of the frequency of replacing the cartridge 40 and adapter 42 combination and depends only on the power consumption of the device 30. The end cap 44 surrounds the base portion 38 with its recess 90 and holds the power source 110 in place using the post 92. The needle-free injecting assembly 34 can then be combined with the fluid delivery assembly 32 with the needle-free syringe 94 passing through the first aperture 52 of the base portion 38 and being received by the cup 74 of the adapter 42. The latch depression 48 and the catch 97 on the needle-free injecting assembly 34 cooperate, either mechanically or magnetically, to couple the fluid delivery assembly 32 to the needle-free injecting assembly 34. At this point, fluid medicine can be delivered from the fluid delivery assembly 32 to the needle-free injecting assembly 34 by rotating the winding sleeve 98. In the illustrated embodiment, the transfer of fluid into the needle-free injecting assembly 34 does not need to be primed because the very small volume of air initially in the adapter 42 and other components of the fluid delivery device 30 is very small. In other embodiments, however, a priming option is used to accommodate for differing designs of the fluid delivery device 30.

Figure 3A:
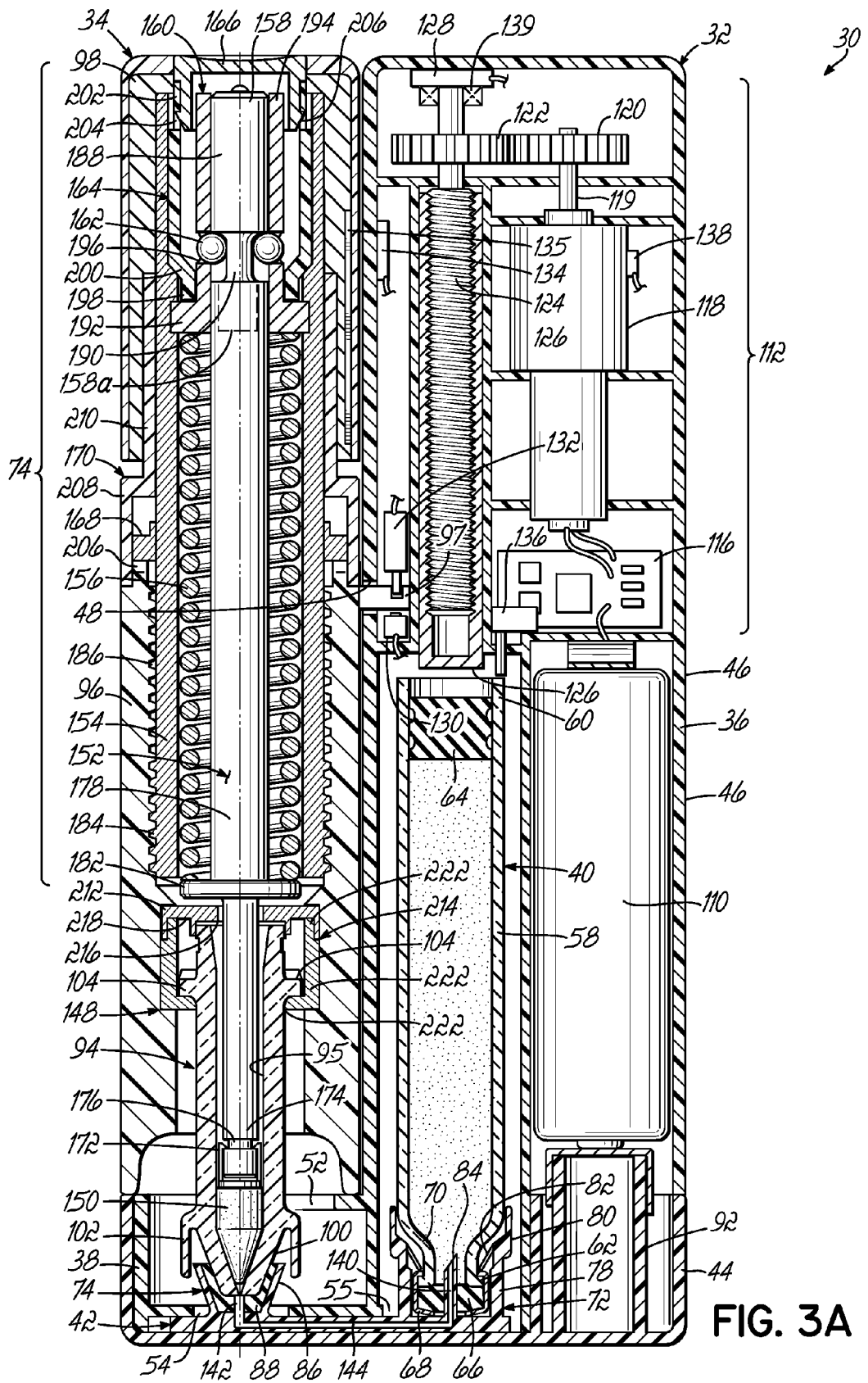
FIG. 3A illustrates a cross-sectional view taken through section 3A-3A of the fluid injection device illustrated in FIG. 1.
Figure 4:
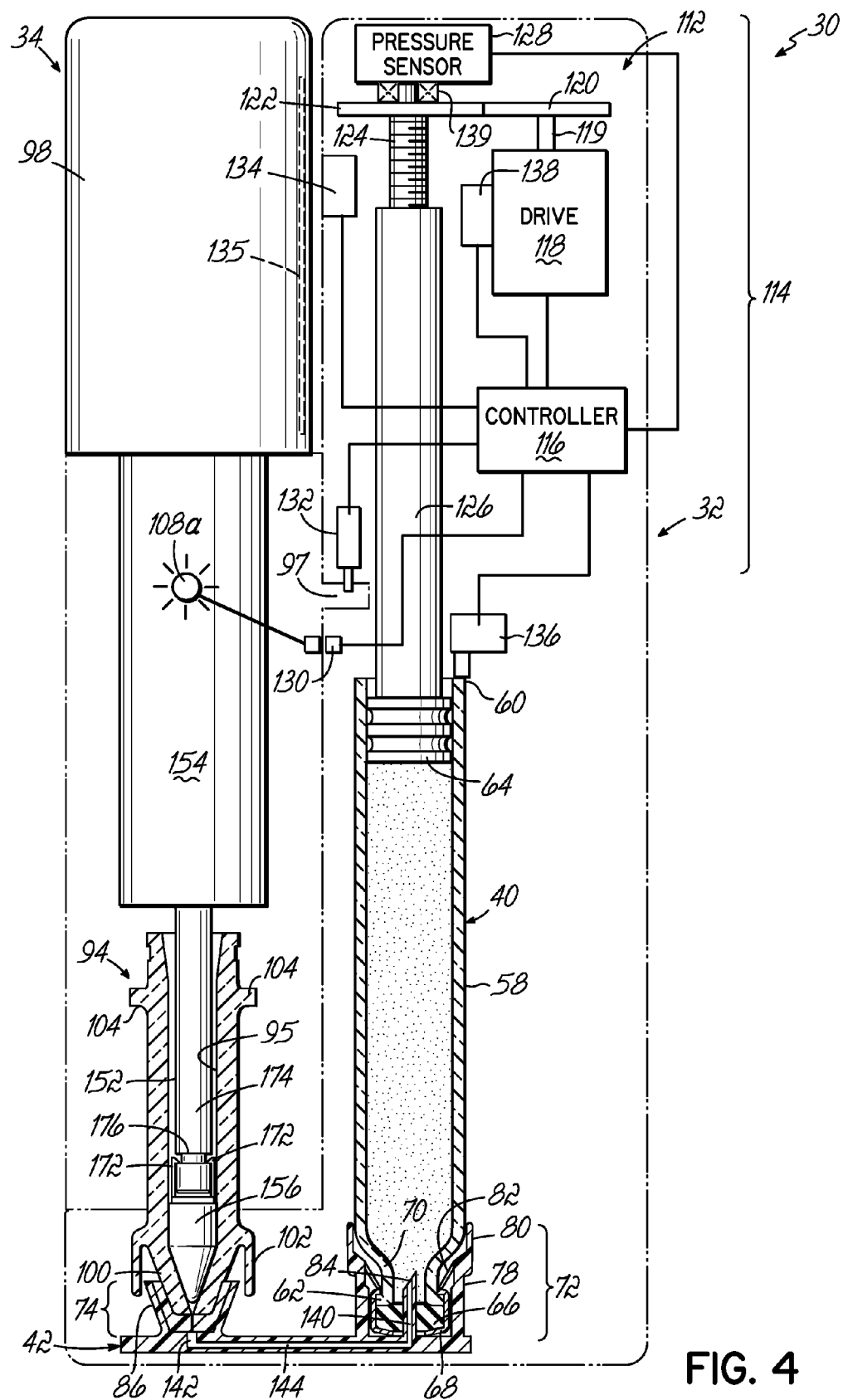
FIG. 4 illustrates a schematic diagram describing the operation of the electronic control system and various sensors while using the fluid injection device of FIG. 1.

Referring to FIG. 3A, additional internal components of the fluid delivery assembly 32 and the needle-free injecting assembly 34 are illustrated. The battery 110 is usually an AA battery, however, those skilled in the art recognize other types of batteries or power sources can be used in other embodiments. The battery 110 powers two main assemblies that are very important in regulating the fluid delivery process. The first assembly is the drive train 112 that is used to apply a force to the movable piston 64 to prevent adhesion or static friction between the movable piston 64 and cartridge body 58 of the cartridge 40, among other functions. The second assembly is illustrated in FIG. 4. The second assembly is the sensing assembly 114 that senses various conditions of the fluid injection device 30 such as whether the fluid delivery assembly 32 is coupled to the needle-free injecting assembly 34, if the remaining dose in the cartridge 40 is insufficient, if too little or too much force is being applied to the movable piston 64, and any other condition that would be readily apparent to those skilled in the art.

Referring to FIG. 3, the drive train 112 is an electro-mechanical assembly that is used to apply a force to the movable piston 64 to prevent adhesion or static friction and assist with controlling the delivery of fluid medicine to the needle-free injecting assembly 34. The drive train 112 includes an electronic control system 116, also part of the sensing assembly 114, that works with the sensing assembly 114 to electronically control the drive train 112, a motor 118 for providing the torque for the drive train 112, a first gear 120 that is coupled to the motor 118, a second gear 122 that is operatively coupled to the first gear 120 and that rotates in response to the first gear 120, an externally threaded member 124 that is operatively coupled to the second gear 122 and rotates in synchronization with the second gear 122, and a nut 126 or actuating element that receives the externally threaded member 124 and contacts the movable piston 64 as it extends in response to the rotation of the externally threaded member 124. The drive train 112 is thereby electronically controlled by the control system 116 controlling the amount of instantaneous torque delivered by the motor 118 to apply a force to the movable piston 64 during delivery of the fluid medicine or at other times, as necessary or desired. The control system 116 controls the amount of instantaneous torque delivered through constant sampling of the torque using sensors for feedback and adjusting the torque accordingly.

The electronic control system 116 includes a programmed central processing unit or microprocessor as part of a printed circuit board assembly. The electronic control system 116 is coupled to the motor 118 to send a signal to begin rotation of the motor 118. The electronic control system 116 is also part of the sensing assembly 114 that is described in more detail hereinbelow with respect to FIG. 4. The electronic control system 116 is powered by the battery 110 and is electronically coupled to the battery 110. The electronic control system 116 is usually housed in a chamber for protection from the elements.

The motor 118 in the illustrated embodiment is a reversible motor. The reversible quality allows the nut 126 to be moved in different directions enabling the transfer of fluid from the fluid delivery assembly 32 to the needle-free injecting assembly 34 as well as transfer from the needle-free injecting assembly 34 to the fluid delivery assembly 32. In addition, the reversible motor 118 allows the nut 126 to be retracted to enable a new cartridge 40 to be inserted after one has been depleted. The motor 118 can be any motor readily apparent to those skilled in the art. The motor 118 includes a shaft 119 around which is secured the first gear 120. Accordingly, when the motor 118 rotates the shaft 119 the first gear 120 is also rotated. The teeth of the first gear 120 are intermeshed with the teeth of the second gear 122 so that when the first gear 120 rotates that rotational energy is translated into the rotation of the second gear 122. The diameters of the first and second gears 120, 122 can be selected by an ordinary skilled artisan in view of other design parameters, such as the pitch of the threading in the nut 126 and externally threaded member 124 to produce the desired movement of the nut 126 and externally threaded member 124. The first and second gears 120, 122 can be constructed out of materials that would be readily apparent to those skilled in this art. Moreover, in other embodiments other types, number, design, or arrangement of gears, drive trains, or drive train members are used.

The second gear 122 is fixed to an end of the externally threaded member 124 so that the rotation of the second gear 122 translates into rotation of the externally threaded member 124. In the illustrated embodiment, the externally threaded member 124 is a screw that has threads having a predetermined pitch that match the pitch of the threads in the nut 126. The externally threaded member 124 is commonly formed of a metal or plastic material, however, other materials can be used. The externally threaded member 124 is fixed to the housing 36 by using a thrust bearing 139 so it can rotate but not translate in any direction. Accordingly, the externally threaded member 124 can rotate in one direction that causes the nut 126 to extend to touch the movable piston 64. Rotation in the opposite direction causes the nut 126 to withdraw away from the movable piston 64. The nut 126 in the illustrated embodiment is designed to enclose the length of the externally threaded member 124 to enable a high degree of extension and withdraw. One end of the nut 126 is open to receive the externally threaded member 124 and threadingly engage the externally threaded member 124. The other end of the nut 126 is closed and contacts the movable piston 64 when extended.

The drive train 112 generally operates to apply a desired force to the movable piston 64. For example, the electronic control system 116 can be configured to ensure that a substantially constant force of around 8 lbf is applied to the movable piston 64. The electronic control system 116 receives input from the sensing assembly 114 that fluid is being delivered to the needle-free injecting assembly 34 or another input requiring movement of the drive train 112. The electronic control system 116 is constantly monitoring the state of the system and the indication that fluid is being delivered into the needle-free injecting assembly 34 results in the motor 118 moving in either a forward or reverse direction. The rotation of the motor 118 begins turning the shaft 119 and the first gear 120 mounted upon the shaft 119. The rotation of the first gear 120 is translated into the rotation of the second gear 122. The second gear 122 is fixed to the externally threaded member 124 and therefore the externally threaded member 124 rotates in synchronization with the second gear 122. The threads of the externally threaded member 124 cooperate with the internal threads of the nut 126 causing the nut 126 to translate in relation to the position of the movable piston 64 and to increase or lessen an applied force. The amount of force to be applied is determined, among other things, by the sensing assembly 114 that is described hereinbelow with respect to FIG. 4.

Referring now to FIG. 4, the sensing assembly 114 is illustrated for detecting various operating conditions of the fluid injection device 30. The sensing assembly 114 generally includes a first sensor 128 for sensing the amount of force that is applied to movable piston 64, a second sensor 130 for sensing if the needle-free injecting assembly 34 is coupled to the fluid delivery assembly 32, a latching device 132 for coupling the needle-free injecting assembly 34 to the fluid delivery assembly 32, a third sensor 134 for sensing and outputting signals for managing the power drain on the fluid delivery device 30, a fourth sensor 136 for determining if a cartridge 40 is present, and a fifth sensor 138 for determining the position of the nut 126. In addition, the sensing assembly 114 includes the electronic control system 116 that provides the logic and electronics to process the sensor outputs and make algorithmic decisions and commands based upon the received inputs. Accordingly, the sensing assembly 114 is an electronic network that enables the fluid injection device 30 to alter its operation based on different operating parameters.

The sensing assembly 114 includes a first sensor 128 that monitors the amount of force that is being applied to the movable piston 64. In different embodiments, the first sensor 128 can sense the force being applied either directly or indirectly. In addition, in some embodiments the first sensor 128 can be a position sensor or some combination of a force sensor and a position sensor. Moreover, the force sensor can operate indirectly such as sensing the linear position of the nut and have an empirical table that correlates that position to the force value. One non-limiting type of position sensor is a position encoder that would be at the nut 126 measuring the linear movement of the nut 126. Another type of position sensor is a rotary encoder that measures the rotation of the nut 126 and outputs a binary code to the control system 116 that can be converted into the corresponding linear displacement of the nut 126. Other types of sensors are used in other embodiments. In some embodiments, the first sensor 128 can be a strain gauge or a membrane pressure sensing element, piezoelectric element, etc., that is placed at the gear head end of the externally threaded member 124 between thrust bearing 139 and housing 36 of fluid delivery assembly 32. In the illustrated embodiment, the first sensor 128 is a strain gauge that is a resistive element force sensor. In other embodiments, the strain gauge is placed on the forward end of the nut 126 and abuts the movable piston 64. The force based strain gauge determines whether the fluid is being pushed or pulled by the needle-free injecting assembly 34 by determining if the force on the movable piston 64 is lessening or increasing. Moreover, in other embodiments, the first sensor 128 senses fluid pressure and is positioned directly within the fluid flow path acting on the movable piston 64. Logic inside of the electronic control system 116 can then determine the force applied to the movable piston 64. Furthermore, other embodiments have a first sensor 128 monitoring the amount of torque experienced by a moving part, such as the motor 118, to determine the amount of force applied to the movable piston 64. Other embodiments have a plurality of first sensor 128 types enabling the microprocessor of the electronic control system 116 to be redundant. The electronic control system 116 processes the signals from the first sensor 128 and then directs the drive train 112 to regulate the force on the movable piston 64 based upon these signals. In addition, if the first sensor 128 senses an "overload" condition where the force applied to the movable piston 64 exceeds a predetermined level, the first sensor 128 sends a signal to the electronic control system 116 to reverse the motor 118 and depressurize the cartridge 40. The amount of depressurization can be complete depressurization to simply depressurizing the cartridge 40 enough to drop the pressure below the predetermined level.

A standard force for application to the movable piston 64 is preprogrammed in the electronic control system 116. The standard force may be empirically determined or optionally by testing each cartridge 40 upon loading into the device 30. The standard force is sufficient to overcome the static friction on the movable piston 64 from the interior of the cartridge 40, either alone or with the assistance of the otherwise usually inadequate vacuum force created by the injecting assembly 34 during transfer of the fluid medicine into the needle-free syringe 94 of the injecting assembly 34. The sensed force is used to automatically adjust the applied force in order to maintain the standard force to transfer the fluid medicine into the needle-free injecting assembly 34 when rotating the winding sleeve 98. In many embodiments, the standard force may range from seven to fifteen pounds. The first sensor 128 monitors the force applied to the movable piston 64 and sends a signal to the electronic control system 116 to change the direction of motor 118 when the force leaves the standard force range.

A dosage reduction force can also be preprogrammed into the electronic control system 116. The dosage reduction force is empirically determined. The dosage reduction force is the amount of force applied to the movable piston 64 when the winding sleeve 98 is rotated to decrease the amount of fluid that has been withdrawn into the needle-free syringe 94. The fluid medicine is urged back into the cartridge 40 increasing hydraulic pressure. The increase in hydraulic pressure increases the force applied to the movable piston 64 and the nut 126. The first sensor 128 measures this force and outputs it to the electronic control system 116. If the force level is equal to or in excess of the empirically determined dosage reduction force the electronic control system 116 sends a signal to the motor 118 to begin withdrawing the nut 126. The hydraulic pressure inside of the cartridge 40 decreases enabling the fluid to flow from the needle-free injecting assembly 34 into the cartridge 40. The nut 126 continues withdrawing until the first sensor 128 senses that the force on the movable piston 64 has returned to the standard force range. Accordingly, the maintenance of a standard force on the movable piston 64 enables the hydraulic pressure of the fluid medicine to remain generally constant.

The sensing assembly 114 includes a second sensor 130 supplying input to the electronic control system 116 concerning the needle-free injecting assembly 34. The second sensor 130 is configured to recognize when the needle-free injecting assembly 34 is coupled to the fluid delivery assembly 32. Thus, delivery of the fluid medicine is prevented until the fluid delivery assembly 32 is coupled to the needle-free injecting assembly 34. In addition, the second sensor 130 provides a signal to the electronic control system 116 during removal of the needle-free injecting assembly 34. This signal enables reversal of the motor 118 lessening the force on the movable piston 64 to depressurize the system prior to removal of needle-free injecting assembly 34. This lowering of pressure assists in preventing both static and transient leakage between the needle-free injecting assembly 34 and the adapter 42. Moreover, in some embodiments, a preload force is applied when the needle-free injecting assembly 34 is coupled to the fluid delivery assembly 32 to assist in the prevention of leaking. In this embodiment, the second sensor 130 can provide a signal when the preload force has been obtained upon coupling the needle-free injecting assembly 34 to the fluid delivery assembly 32.

The second sensor 130 can take a variety of forms, such as, but not limited to, a magnet having a sensor that indicates when another magnet is proximate. For example, in the illustrated embodiment the second sensor 130 magnetically contacts a corresponding magnet on the needle-free injecting assembly 34 causing the indicator light 108 to illuminate. Thus, the indicator light 108 indicates the docking status of the needle-free injecting assembly 34. Moreover, the second sensor 130 sends a signal to the electronic control system 116 to actuate the latching device 132 inside of the latch depression 48 into a cooperating recess in the needle-free injecting assembly 34. Therefore, the second sensor 130 is used to ensure that the fluid delivery assembly 32 and needle-free injecting assembly 34 are rigidly coupled. The second sensor 130 can posses other forms in other embodiments, such as an optical sensor, a wireless telemetry module that communicates with the needle-free injecting assembly 34, or other form.

In addition, the sensing assembly 114 of the illustrated embodiment includes a third sensor 134 supplying input to the electronic control system 116 to manage the power drain on the fluid injection device 30. Like the second sensor 130, the third sensor 134 can take a variety forms, such as, but not limited to, an electrical switch, or a magnetic switch, or an optical or infrared switch, or inductive switch, or telemetry module in the form of a receiver that wirelessly communicates with a transmitter of the needle-free injecting assembly 34. In the illustrated embodiment, the third sensor 134 is a telemetry module wirelessly communicating with a transmitter 135 in the winding sleeve 98 of the needle-free injecting assembly 34. The third sensor 134 follows the rotation of the winding sleeve 98 and also can indicate whether the needle-free injecting assembly 34 has been removed. Information related to the rotation of the winding sleeve 98 is communicated to the electronic control system 116 for managing the power drain on the fluid delivery device. For example, if there hasn't been rotation of the winding sleeve 98 or removal of the needle-free injecting assembly 34 over a predetermined time period, such as five minutes or the like, the third sensor 134 can send a signal to the electronic control system 116 to move into a sleep mode. In the sleep mode, the pressure against the movable piston 64 can be lessened or removed to reduce the power drain and the potential for any fluid leakage. Moreover, the other electronic components can reduce their power consumption in any manner readily apparent to those skilled in the art. Immediately after the needle-free injection assembly 34 has been coupled with fluid delivery assembly 32 or when the winding sleeve 98 is rotated the third sensor 134 can signal the electronic control system 116 to "wake-up" and assume normal operation and pressurize the cartridge 40. The third sensor 134 outputs in many embodiments are combined with the second sensor 130 outputs. The second sensor 130 can indicate if the needle-free injecting assembly 34 is not coupled to the fluid delivery assembly 32 thereby providing a check on whether the fluid delivery should be started and preventing incorrect readings by the third sensor 134.

The sensing assembly 114 also includes a fourth sensor 136 for sensing the presence of a cartridge 40. Additionally, in some alternate embodiments the fourth sensor 136 can be configured to recognize if the end cap 44 is in place. The fourth sensor 136 is positioned to be in contact with the cartridge 40 when the cartridge 40 has been inserted into the housing 36 of the fluid delivery assembly 32. The fourth sensor 136 could be any sensor known to those skilled in the art for recognizing physical contact and converting it into an electrical output. The positioning of the fourth sensor 136 is designed so that the cartridge 40 will come in contact with the fourth sensor 136 after the adapter 42 has forced the cartridge 40 against the fourth sensor 136. The presence of a loaded cartridge 40 can be indicated in any manner readily apparent to those skilled in the art.

The sensing assembly 114 includes a fifth sensor 138 for sensing the amount of extension of the nut 126. This is useful to determine when a new cartridge 40 is needed or when to shut off the motor 118 because the nut is either fully extended or withdrawn. In the illustrated embodiment, the fifth sensor 138 is a sensor or encoder that tracks the operation of the motor 118 to determine the amount of revolutions of the motor 118. The number of revolutions of the motor 118 can be fixed to the number of revolutions of the externally threaded member 124 and the nut 126 using logic in the electronic control system 116. The exhaustion of the cartridge 40 can be communicated to the user in a variety of ways, such as an indicating light or display on the fluid delivery assembly 32 or the needle-free injecting assembly 34. The indicating lights or displays in some embodiments are Light Emitting Diode (LED) lights or displays. Other embodiments use incandescent lights or other types of illumination. In one embodiment, the indicator light 108 indicates when the cartridge 40 needs to be replaced. The light or display can change colors in some embodiments as the cartridge 40 empties over time, in other embodiments the light or display blinks at a faster or slower rate depending upon the amount of fluid medicine present in the cartridge 40. Some embodiments have a series of successive lights that each indicates the fraction of the fluid that is left. Those skilled in the art therefore recognize that there are a variety of methods in which the dispensing of fluid from the cartridge 40 can be indicated based on output from the fifth sensor 138 to the electronic control system 116.

The sensing assembly 114 assists in determining if the proper force is being applied to the movable piston 64 among other functions, however, the adapter 42 enables the physical transfer of the fluid from the fluid delivery assembly 32 to the needle-free injecting assembly 34. Referring back to FIG. 3A, the figure illustrates that upon assembly of the fluid injection device 30, the adapter 42 receives the needle-free syringe 94 in the cup 74. In addition, the adapter 42 also receives the cartridge 40 in the receiving structure 72. The adapter 42 is in fluid communication with the cartridge 40 because the piercing member 84 has pierced the elastomeric septum 66 and a first passage 140 defined inside of the piercing member 84 connects the fluid medicine inside the cartridge 40 with the adapter 42. The adapter 42 is in fluid communication with the needle-free injecting assembly 34 because the opening of the needle-free syringe 94 is aligned with a second passage 142 defined through the inner seal 88 and the outer portion 86 of the cup 74. Fluidly coupling the first passage 140 to the second passage 142 is a third passage 144 that is transverse to both the first passage 140 and the second passage 142 and to an axis through the needle-free injecting assembly 34 passing through the length of the needle-free syringe 94. The third passage 144 enables fluid medicine to be transferred between the needle-free injecting assembly 34 and the fluid delivery assembly 32 in a side-by-side arrangement.

Figure 3B:
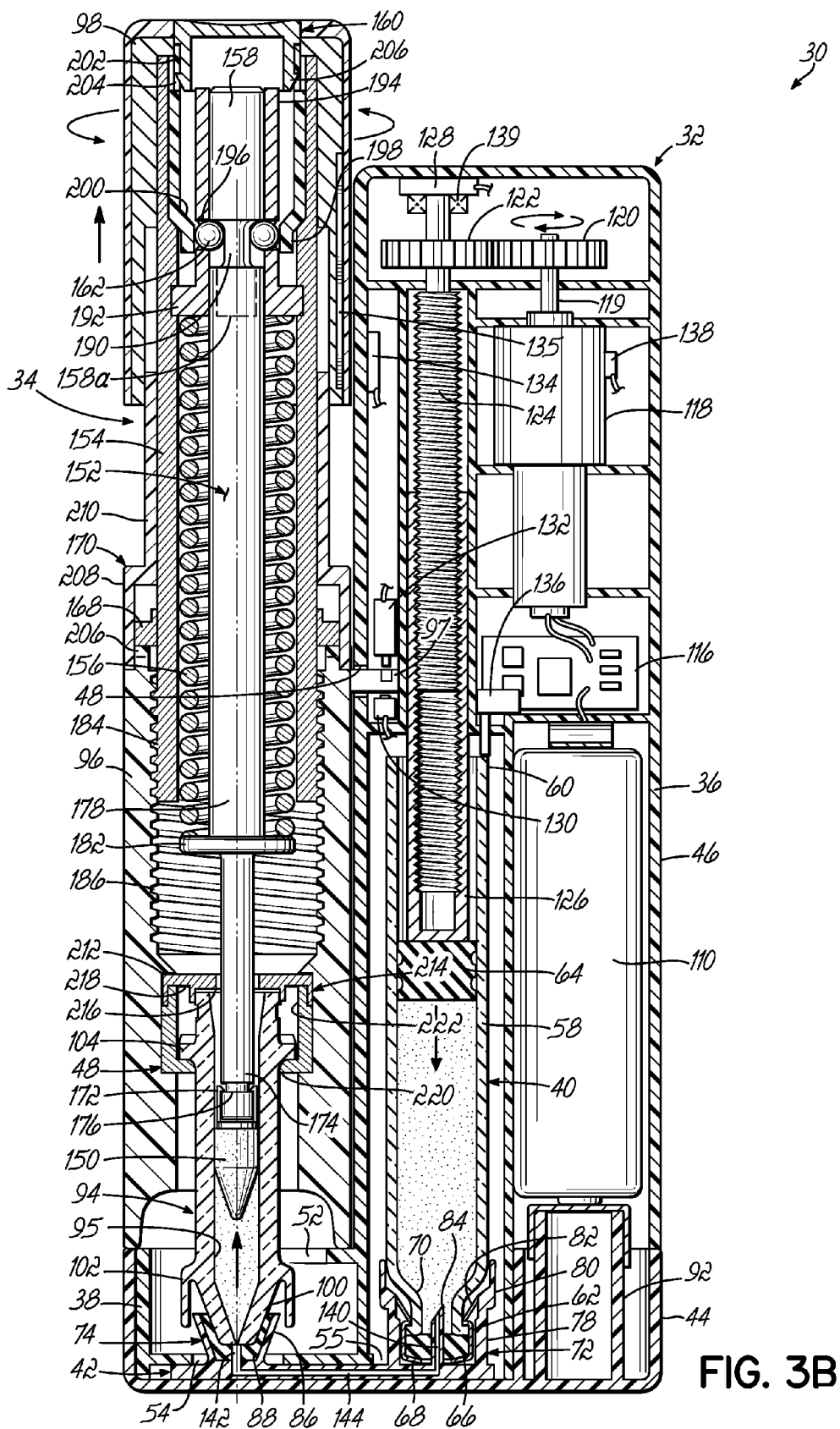
FIG. 3B illustrates a cross-sectional view of the fluid injection device of FIG. 1 similar to the cross-section illustrated in FIG. 3A but further depicting a fluid dose being transferred from the fluid delivery assembly into the needle-free injecting assembly.

The interior components of the needle-free injecting assembly 34 are illustrated in FIGS. 3A and 3B. FIG. 2 discussed the needle-free syringe 94, the injection housing 96 and the winding sleeve 98 of the needle-free injecting assembly 34. The interior component of the needle-free injecting assembly 34 are the power pack assembly 146 and the retaining assembly 148 which are illustrated in FIG. 3A. The power pack assembly 146 is a set of components that cooperate to drive the fluid dose obtained from the fluid delivery assembly 32 into the body. The retaining assembly 148 is a set of components that cooperate to restrain the needle-free syringe 94 and the components that drive the fluid medicine during injection.

The power pack assembly 146 is designed to inject the fluid dose into the body. The needle-free syringe 94 contains a plunger 150 that is in contact with the fluid dose and drives it out of the opening of the needle-free syringe 94. The power pack assembly 146 contains a ram 152 that is coupled to the plunger 150 for driving the plunger 150 into the tapered end 100 of the needle-free syringe 94, a dosage sleeve 154 for containing the other components, a spring 156 for providing the energy to drive the ram 152, a latch rod 158 coupled to the ram 152 for extending the length of the ram 152 and designed to facilitate latching and unlatching the combination of the latch rod 158 and the ram 152, a latch housing 160 for holding ball bearings 162 that restrain the latch rod 158 prior to injection, a button 164 and button cap 166 combination for moving the ball bearings 162 into a position that unlatches the latch rod 158 during the injection, a dosage detent 168 for surrounding and assisting the dosage sleeve 154 in settling into a location for providing a predetermined fluid dose, and a retainer cap 170 that is fixed to the injection housing 96 for connecting the winding sleeve 98 and the injection housing 96.

The plunger 150 is configured for receipt by the tapered end 100 of the needle-free syringe 94. The plunger 150 of the illustrated embodiment is composed of two pieces one of which is a sealing member and the other of which provides a rigid structure for connection with the ram 152. In one embodiment of the illustrated plunger 150 a hard plastic forms the rigid structure. An elastomer to provide a sealing surface can be overmolded or configured in any of several means to form a seal. Other embodiments that promote the movement of fluid in the needle-free syringe 94 are possible. The plunger 150 includes clips 172 that are resilient and snap down to couple the plunger 150 to the ram 152. The illustrated embodiment includes two clips 172, however, those skilled in the art recognize other numbers and designs of clips 172 are used in other embodiments. In addition, in some other embodiments the plunger 150 is formed integrally with the ram 152. The ram 152 is used to drive the plunger 150 down into the tapered end 100 of the needle-free syringe 94. The ram 152 is a long member that extends for a significant portion of the needle-free injecting assembly 34. The ram 152 includes a first portion 174 that includes a groove 176 defined around the periphery of the first portion 174. The groove 176 is designed to receive the clips 172 of the plunger 150 to enable the coupling of the plunger 150 to the ram 152. The ram 152 also includes a second portion 178 that is coupled to the latch rod 158. The ram 152 also includes a plate 182 that is used to restrain the ram 152. The plate 182 contacts the restraining assembly 148 to prevent the ram 152 from becoming a projectile if the injecting assembly 96 is triggered without a needle-free syringe 94.

The dosage sleeve 154 provides structure to contain the ram 152 in the interior of the injection housing 96. The dosage sleeve 154 is a tube commonly formed of a high strength plastic, but other materials can be used in other embodiments. The dosage sleeve 154 includes external threads 184 that cooperate with internal threads 186 of the injection housing 96. The dosage sleeve 154 is also fixed to the winding sleeve 98 so that when the winding sleeve 98 is rotated the dosage sleeve 154 rotates inside of the injection housing 96. The rotation of the dosage sleeve 154 causes the dosage sleeve 154 to translate away and towards the cup 74 because of the internal and external threads 184, 186. The ram 152 and the plunger 150 are also drawn away from the tapered end 100 of the needle-free syringe 94 by this translation creating a vacuum inside of the needle-free syringe 94. This vacuum begins the transfer of fluid medicine from the cartridge 40 into the needle-free syringe 94. Therefore, the rotation of the winding sleeve 98 is transformed into the drawing or returning of a fluid dose from the fluid delivery assembly 32. The spring 156 provides the energy to drive the ram 152 and the plunger 150. The spring 156 is positioned in a compressed orientation having a significant amount of potential energy. The spring 156 can be made of any suitable material, such as a metal or a plastic material. The spring 156 surrounds the ram 152. On its outer surface, the spring 156 is bounded by the dosage sleeve 154. The dosage sleeve 154 is not attached to the spring 156 in any way thereby allowing the dosage sleeve 154 to rotate around the spring 156. The spring 156 is further bounded on one side by the plate 182 of the ram 152 and on the other side by the latch housing 160. The spring 156 is therefore kept in a compressed state until injection. Like the ram 152 and the plunger 150, during dose setting the spring 156 moves laterally away from the tapered end 100 of the needle-free syringe 94 creating an area between the end of the dosage sleeve 154 and the restraining assembly 148 that the spring 156 can expand into upon injection as shown in FIG. 3B. The latch rod 158 includes a first threaded end 158a coupled to second portion 178 of ram 152. The combination of the latch rod 158 and the ram 152 translates during injection. Different materials may be used for fabrication of the ram 152 and latch rod 158 as the latch rod 158 may require a higher degree of hardness than is necessary for the ram 152. A curved necked portion 190 of the latch rod 158 is constructed for receiving the ball bearings 162. Prior to injection, the latch rod 158 is restrained by the ball bearings 162. During injection, the latch rod 158 is no longer restrained by the ball bearings 162. Thus, the ram 152 and the plunger 150 are driven towards the tapered end 100 of the needle-free syringe 94 by the spring 156.

The latch housing 160 is fixed to the dosage sleeve 154 and surrounds the latch rod 158. The latch housing 160 has an inner passageway that begins at a first end 192 and terminates at a second end 194. The first end 192 is flanged to create a surface to restrain the spring 156. The second end 194 is not flanged facilitating the button cap 166 passing around the second end 194. The latch housing 158 also includes holes 196 that allow the ball bearings 162 to move in and out. The ball bearings 162 move into the holes 196 when the button 164 and button cap 166 combination is unpressed. The button 164 in this position urges the ball bearings 162 into the holes 196 and into the curved neck portion 190 of the latch rod 158. The ball bearings 162 move out of the holes 196 when the button 164 and button cap 166 is pressed. When the button cap 166 is pressed, the ball bearings 162 roll out of the curved neck portion 190 because the spring 156 is driving the latch rod 158 towards the tapered end 100 of the needle-free syringe 94.

The button 164 can move the ball bearings 162 into or out of the holes 196 of the latch housing 158 depending on the position of the button 164. The button 164 is combined with the button cap 166 providing a combination that triggers the injection. The button 164 has a first end 198 that is open that slidably retains the latch rod 158 and latch housing 160. The interior annular surface 200 of the first end 198 bias the ball bearings 162 into the holes 196 of the latch housing 160 when the button 164 and button cap 166 are not pressed. During injection, the button 164 and button cap 166 are pressed by the user moving the button 164 towards the tapered end 100 of the needle-free syringe 94. Thus, the ball bearings 162 move away from the curved neck portion 190 of the latch rod 158 and into the interior of the button 164 and rest against the tapered surfaces 201.

The ball bearings 162 are able to move because they are no longer aligned with the annular surface 200. The interior of the button 164 contains the latch housing 160 and the latch rod 158, however, there is space between the latch housing 160 and the button 164 to allow the ball bearings 162 to move outward into the area when the button 164 is depressed. In the illustrated embodiment, however, the amount of space between the button 164 and the latch housing 160 is smaller than the diameter of the ball bearings 162 to prevent the ball bearings 162 from rolling any further. The button 164 also includes a second end 202 that includes notches 204 for receiving the button cap 166. The button cap 166 includes flanges 206 that are received by the notches 204 to couple the button cap 166 and the button 164 together. The button cap 166 is pressed by the user to initiate the injection process. The button cap 166 has an interior space that is large enough to wrap around the latch housing 160 but has a tapered portion 208 that can be received by the second end 202 of the button 164. The combination of the button 164 and the button cap 166 move together to release the latch rod 158 during injection.

The power pack assembly 146 also includes a dosage detent 168 that is coupled to the dosage sleeve 154. The dosage detent 168 has nubs 169 (best shown in FIGS. 3C and 3D) that couple it to dosage sleeve 154 so that when the dosage sleeve 154 rotates the dosage detent 168 rotates with the dosage sleeve 154. The dosage detent 168 also includes spikes (not shown) that couple with the outer rim 206 of the injection housing 96. The outer rim 206 of the injection housing 96 of the illustrated embodiment includes six notches (not shown) that are positioned at 60° relative to each other around the circumference of the outer rim 206. These notches are designed to receive the spikes so that the rotation of the winding sleeve 98 and correspondingly the dosage sleeve 154 will catch every 60°. A predetermined unit dose is correlated to the 60° rotation. For one example, at one unit of fluid medicine the two spikes would be located at 30° counter-clockwise and 210° counterclockwise from an imaginary 12 o' clock position. Then at two units of fluid medicine the spikes would be located at 90° counterclockwise and 270° counterclockwise and so on. The combination of the spikes and the notches of the outer rim 206 results in having a certain unit of medicine corresponding to a certain amount of rotation. The injecting of a dose between units of medicine is discouraged by this design.

The power pack assembly 146 also includes a retainer cap 170. The retainer cap 170 includes a base portion 208 and a tubular portion 210. The base portion 208 is designed to form fit over the injection housing 96 and receive the outer rim 206 and lie flush with the outer surface 46 of the injection housing 96. The base portion 208 is fixed to the injection housing 96 using Allen screws. In the illustrated embodiment, the base portion 208 also surrounds the dosage detent 168. The tubular portion 210 is surrounded on the outside by the winding sleeve 98 and allows the winding sleeve 98 to translate as it rotates without exposing any of the interior components of the needle-free injecting assembly 34. The tubular portion 210 contains the dosage sleeve 154 and also enables the dosage sleeve 154 to translate while it rotates. The retainer cap 170 is not threaded and therefore is a limit on the amount of translational movement the dosage sleeve 154 can travel.

The needle-free injecting assembly 34 also includes the restraining assembly 148. Furthermore, the restraining assembly 148 restrains the movement of the needle-free syringe 94 during fluid delivery and injection. The restraining assembly 148 includes two main portions. The first portion is a retainer plate 212 for restricting the movement of the ram 152 (when the needle free syringe 94 is not attached) and plunger 150 and an acceptor 214 that is coupled to the retainer plate 214 that restricts the needle-free syringe 94 and provide support for the retainer plate 212. The retainer plate 212 is disk shaped and includes an opening 216 through the center that allows the ram 152 to pass through. The retainer plate 212 also includes a groove 218 around the outer surface that is designed to receive the acceptor 214. The acceptor 214 also includes an opening 220 that allows the needle-free syringe 94 to be received on one side and the ram 152 to pass through. The acceptor 214 includes flanges 222 that are received by the groove 218 of the retainer plate 212 to complete the restraining assembly 214. Furthermore, the restraining assembly 146 cooperates with the flanges 104 of the needle-free syringe 94 to restrain the needle-free syringe 94 during fluid delivery or injection.

Referring now to FIG. 3B, the delivering of the fluid medicine from the cartridge 40 of the fluid delivery assembly 34 to the needle-free syringe 94 of the needle-free injecting assembly 34 is illustrated. Initially, a user rotates the winding sleeve 98 as illustrated by the arrows. Rotation of the winding sleeve 98 also rotates the dosage sleeve 154 inside of the injection housing 96 and the internal and external threads 184, 186 cooperate to cause the dosage sleeve 154 to translate in predetermined amount determined by the concurrent rotation of the dosage detent 168. The user selects the correct units of dose to be injected and continues to rotate the winding sleeve 98 until that dosage is obtained. The latch housing 160 is coupled to the dosage sleeve 154 and therefore also translates as the dosage sleeve 154 translates away from the tapered end 100 of the needle-free syringe 94. The button 164 maintains bias on the ball bearings 162 keeping them inside of holes 196 and therefore they also translate with the latch housing 160. The ball bearings 162 are coupled to the latch rod 158 and cause it to translate which correspondingly causes the ram 152 and plunger 150 to translate because they are coupled to the latch rod 158. This increases the area between the plate 182 and the retainer plate 212. The translation of the ram 152 and the plunger 150 creates a vacuum in the interior 95 or reservoir of the needle-free syringe 94. The vacuum pulls fluid out of the cartridge 40, through the first passage 140, the third passage 144, and the second passage 142 and into the needle-free syringe 94. Simultaneously, the sensing assembly 114 receives an input from the first sensor 128 to apply a force to the movable piston 64 through operation of drive train 112. The drive train 112 moves and causes the nut 126 to apply a force to the movable piston 64 to overcome adhesion or static friction and to maintain a standard force to assist with the delivery of the fluid. Accordingly, fluid is delivered to the needle-free injecting assembly 34 for injection in a proper amount and without spillage. The transfer of the fluid into the needle-free injecting assembly 34 can be visually confirmed in some embodiments. For example, graduated markings can be placed on the portion of the needle-free syringe 94 that protrudes from the bottom of the needle-free injecting assembly 34. In addition, in alternate embodiments, the transfer of fluid can be indicated through electronic methods. For example, in one embodiment a light can flash to indicate that the fluid has transferred. Additional sensors can be added to the sensing assembly 114 to provide outputs relating to the amount of fluid that has entered into the needle-free syringe 94. In some embodiments, the control system 116 can take the outputs from the additional sensors and convert them into a display indicating the amount of fluid that has transferred.

Figure 3C:
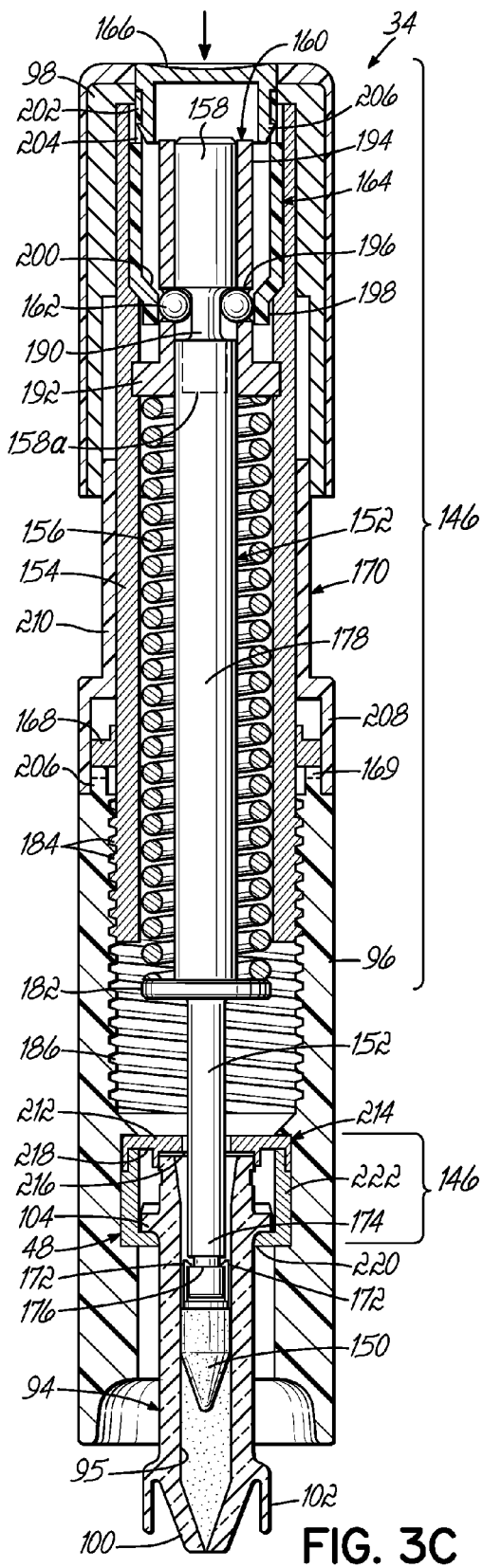
FIG. 3C illustrates a cross-sectional view of only the needle-free injecting assembly of FIG. 1 similar to the cross-section illustrated in FIG. 3A and depicting a fluid dose inside the needle-free injecting assembly ready for injecting into the body.

Referring now to FIG. 3C the needle-free injecting assembly 34 is illustrated after the fluid dose has been transferred into the needle-free syringe 94. This figure illustrates that space remains between plate 182 and the retainer plate 212 that can be filled by the spring 156 once the latch rod 154 is no longer coupled to the latch housing 160 using the ball bearings 162. Thus, the fluid dose is ready to be injected into the body.

Figure 3D:
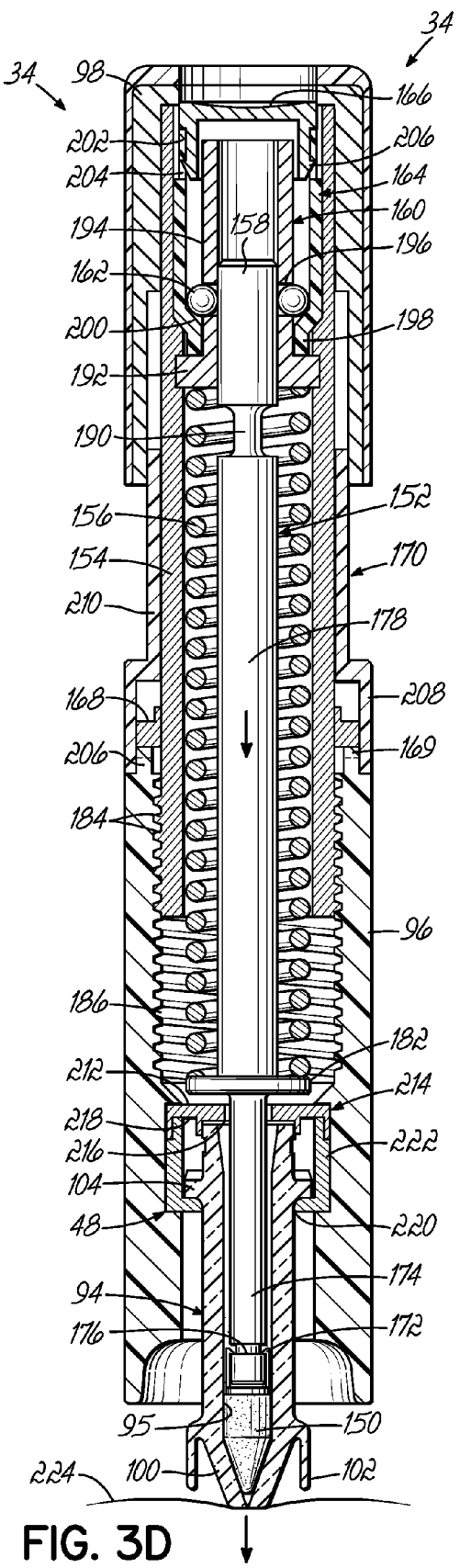
FIG. 3D illustrates a cross-sectional view of the needle-free injecting assembly of FIG. 1 similar to the cross section illustrated in FIG. 3C and depicting a fluid dose being injected into the body.

FIG. 3D illustrates the needle-free injecting assembly 34 injecting fluid into a body 224. The injection occurs by the user placing the tapered end 100 of the needle-free syringe 94 upon the body 224 and pressing the button cap 166. Pressing the button cap 166 pushes the button cap 166 and therefore the button 164 towards the tapered end 100 of the needle-free syringe 94. As the button 164 moves in this direction, the annular surface 200 no longer biases the ball bearings 162 into the holes 196 of the latch housing 160. The ball bearings 162 roll slightly out of the holes 196 into the interior of the button 164 because of the tapering outward from the first end 198. The interior of the button 164, however, is not wide enough to have the ball bearings 162 roll completely inside and they are pressed against the tapered surfaces 201. The ball bearings 162 no longer are contained by the curved neck portion 190 of the latch rod 158 and roll out of the holes 196. The latch rod 158 therefore is no longer restrained by the ball bearings 162 and is free to translate towards the tapered end 100 of the needle-free syringe 94. The spring 156 can now extend and release all of its potential energy and thus presses against the plate 182 of the ram 152. The latch rod 158, ram 152, and plunger 150 are rapidly moved towards the tapered end 100 of the needle-free syringe 94 as the spring 156 expands closing the gap between the plate 182 and the retainer plate 212. The plunger 156 pushes the fluid medicine quickly and with a large force. The small opening in the tapered end 100 of the needle-free syringe 94 causes the fluid to further accelerate into a high velocity jet that penetrates below the skin of the body without having to puncture the skin. The motion of the ram 152 is stopped when the plunger 150 reaches the bottom of the needle-free syringe 94. Afterward, the user can rotate the winding sleeve 98 in the opposite direction to cause the dosage sleeve 154 to translate completely in the other direction and cause the button 164 and button cap 166 to resume their original position.

Figure 5:
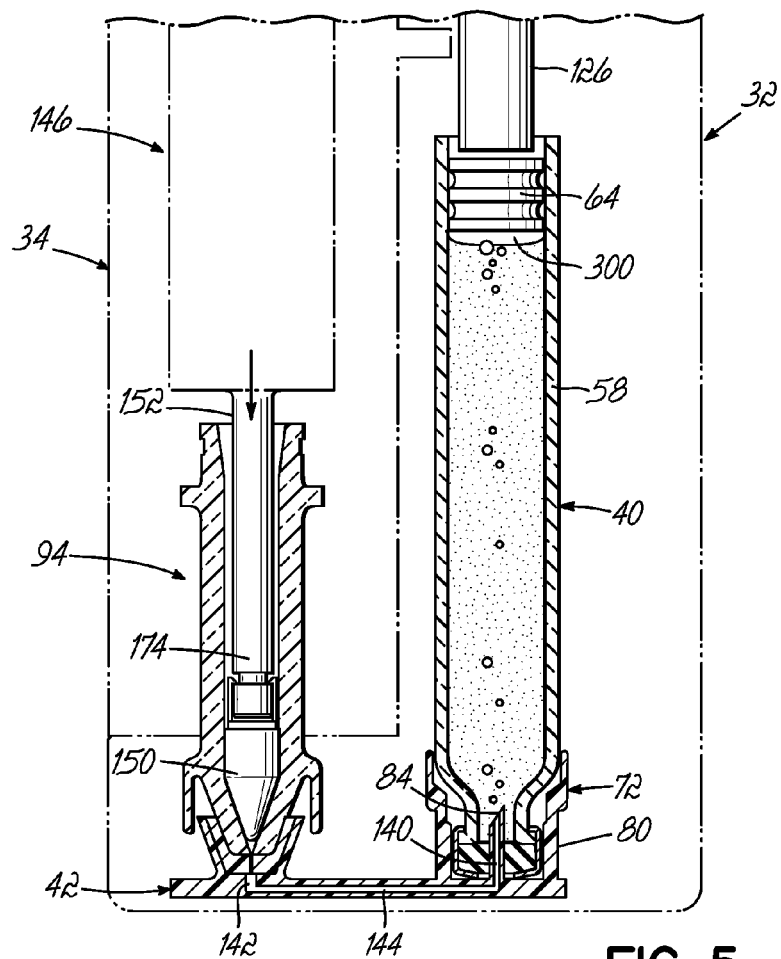
FIG. 5 schematically illustrates an alternative embodiment of a side-by-side needle-free fluid injection device utilizing injected air in a cartridge for subsequent use in assisting the withdrawal of liquid out of the fluid delivery assembly.

FIG. 5 illustrates an alternative method for assisting the withdrawal of fluid from a fluid delivery assembly or mechanism 32, including a cartridge 40 and a piston 64. In this embodiment, it will be noted that the motorized assist device as described above has been eliminated, however, it will be appreciated that the assist method described in connection with FIG. 5 may be applied as either an additional or an alternative assist method to any other assist method. Reference numerals used in FIG. 5, as well as the figures that follow, which are identical to those used in any previous figure, refer to previously described structure and therefore require no further description. However, this does not apply to nut 126 which, in this configuration, will be a fixed element in contact with the piston 64 to prevent piston 64 movement in the upward direction. For purposes of clarity, unnecessary details have been eliminated from FIG. 5 and the other figures that follow. FIG. 5 generally illustrates the concept of using an injected priming bolus of air 300 within the cartridge 40 to act as a spring to reduce backpressure within the cartridge 40. That is, the air 300 injected into the cartridge 40 provides a compressible spring-like element within the fluid and, therefore, accommodates the flow of medicinal fluid into the needle-free syringe 94 by pressurizing the cartridge 40, as viewed in FIG. 5. The air 300 may be injected in any suitable manner. The manner schematically illustrated generally comprises moving the plunger 150 downward to inject the air through the passageways 140, 142, 144 leading to the interior of the cartridge 40. As an example, 0.15 ml of air, equivalent to 15 units of volume in the needle-free syringe 94, may be introduced into the cartridge 40. Of course, this would necessitate an initially retracted position of the plunger 150 sufficient to draw a desired amount of air 300 such as 15 units, for example, into the needle-free syringe 94. The air beneath the plunger 150 may then be pushed through the passages 140, 142, 144 and into the cartridge 40. This can be done with the needle-free injecting assembly 34 separated from the fluid delivery assembly 32 and by rotating the winding sleeve 98 of the needle-free injecting assembly 34 sufficiently to visually verify 15 units drawn as seen in the dosage window 106 of the needle-free injecting assembly 34. Subsequent dosing procedures can add additional amounts of air 300.

Figure 6:
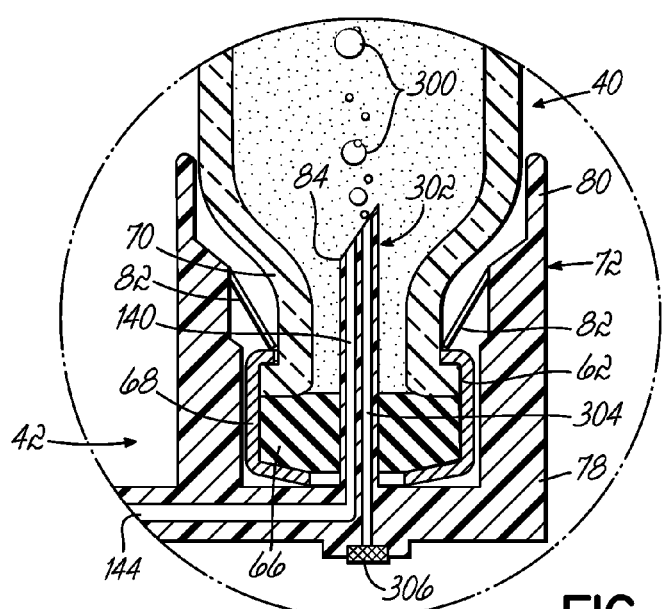
FIG. 6 is an enlarged cross sectional view of a lower portion of the fluid delivery assembly illustrating an alternative fluid delivery system including a modified adapter.

FIG. 6 illustrates another alternative method of injecting air 300 into the cartridge 40 through a modified piercing member 302. In this regard, the piercing member 302 includes a first portion 84 with a first passage 140 for withdrawing the fluid from the cartridge 40 and directing the fluid into a passageway 144 in the adapter 42. A second passage 304 is provided in the piercing member 302 and leads to a suitable combination check valve-filter element 306 communicating with atmosphere. As fluid is withdrawn from the cartridge 40 through the first passage 140, air 300 is directed into the cartridge 40 through the filter element 306 and the second passage 304, to displace a desired dosage of the medicinal fluid with air 300 and enable transfer of the fluid into the needle-free syringe 94. Depending on the breakpressure of the checkvalve 306, piston 64 may or may not move downward during fluid transfer.

Figures 7A, 7B, 7C:
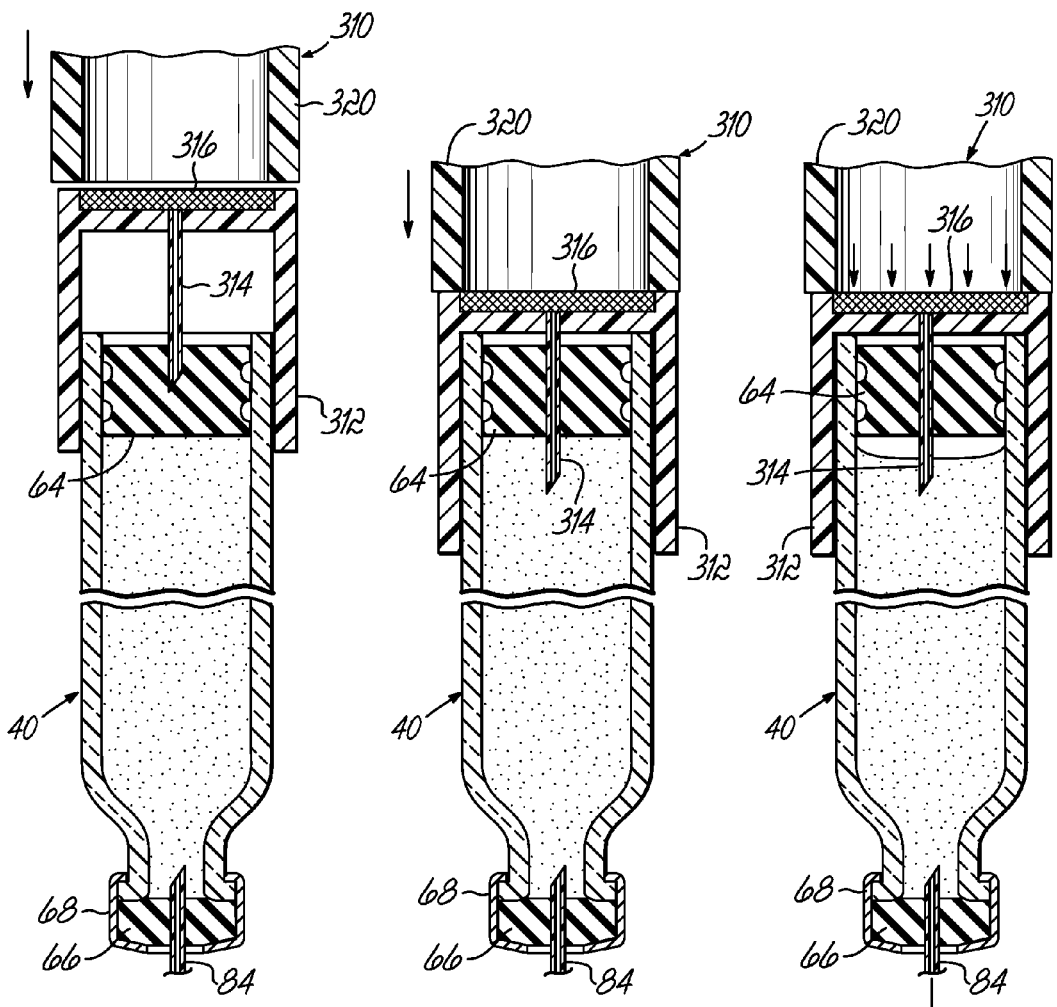
FIGS. 7A-7C are cross sectional views of another alternative fluid delivery assembly utilizing a filtered air injection component.

FIGS. 7A-7C illustrate a fluid delivery cartridge 40 having another modified or alternative mechanism for introducing air into the cartridge 40 for generally the same purposes as described above in connection with FIG. 5. In this series of figures, an air introducing mechanism 310 is schematically shown and includes a housing 312 carrying a needle 314 and a suitable air filter element 316. An actuating member or portion 320 is provided for depressing the housing 312 and its associated needle 314 and filter element 316. As shown in FIG. 7B, this causes the needle 314 to penetrate the piston 64 such that the open end of the needle 314 communicates with the fluid within the cartridge 40. As the fluid within the cartridge 40 is withdrawn from the cartridge 40 via the piercing member 84, air from the atmosphere is directed through the filter element 316 and the passage within the needle 314 to create a priming bolus of air 300 within the cartridge 40 as shown in FIG. 7C. Again, the purpose of the bolus of air 300 is generally the same as described above in connection with FIG. 5. Note that similar to the previous two alternative approaches, piston 64 may or may not move during medicinal fluid displacement/delivery.

Figure 8A:
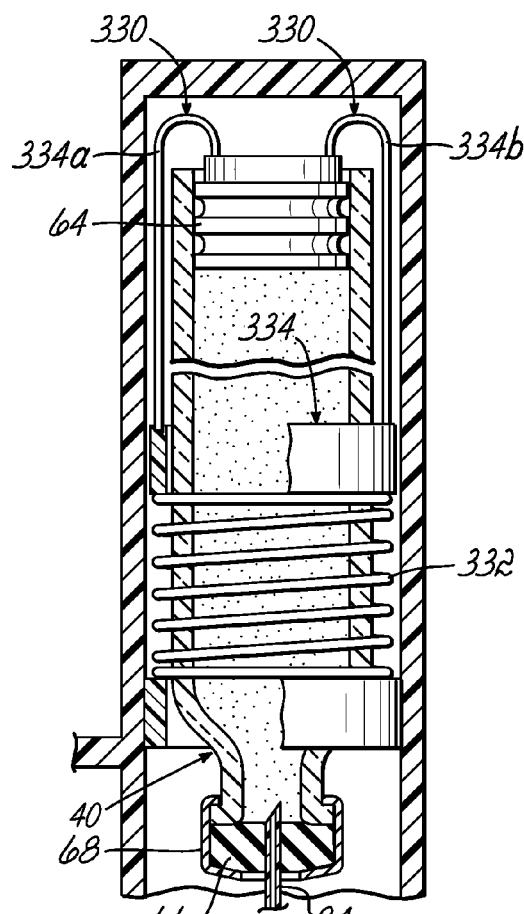
FIGS. 8A and 8B are respective cross sectional views of another alternative fluid delivery assembly utilizing a spring actuated assist device integrated with a flexible tape drive mechanism.
Figure 8B:
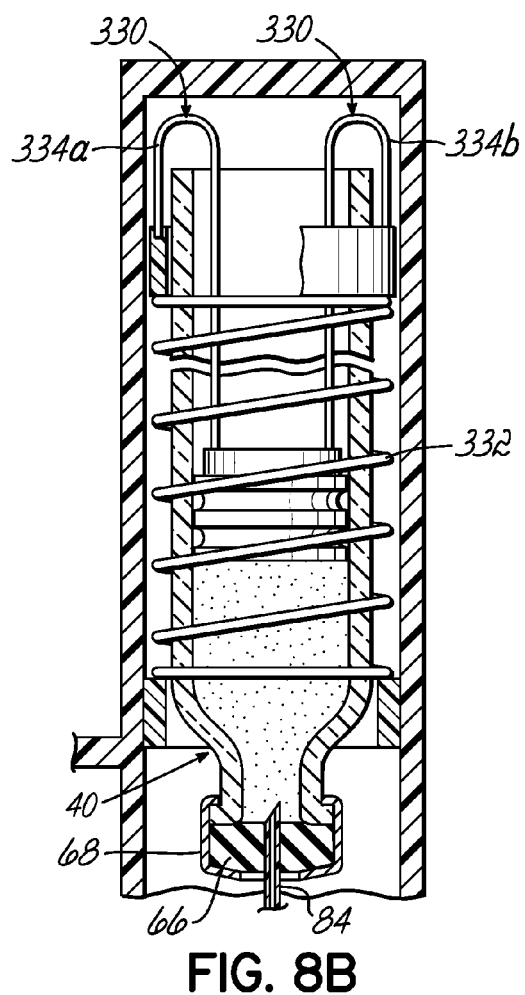

FIGS. 8A and 8B illustrate another alternative mechanism 330 for assisting movement of the piston 64 during withdrawal of fluid from a cartridge associated with a fluid delivery mechanism. In this schematically illustrated assist device, a spring 332 is utilized in connection with a tape drive 334. In FIG. 8, the spring 332 is compressed and therefore provides an upward force on the tape drive 334. The tape drive 334 converts this into a downward force on the piston 64 at the ends of the tape elements 334a, 334b. This downward force is used as an assistive force on the plunger 64 as the fluid within the cartridge 40 is withdrawn through the piercing member 84.

Figure 9:
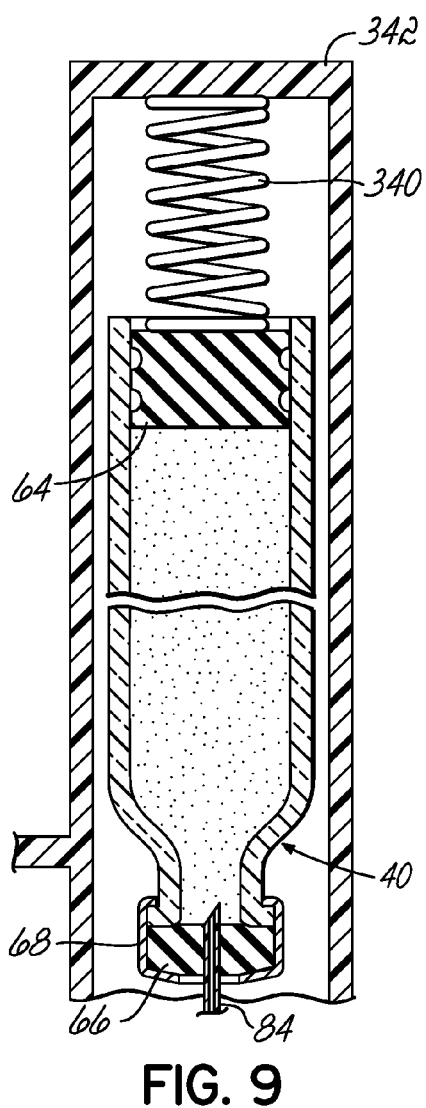
FIG. 9 is another schematic cross sectional view of another alternative fluid delivery assembly utilizing a spring activated assist device.

FIG. 9 illustrates another alternative embodiment of a fluid delivery assist device using similar principles to those discussed in connection with FIGS. 8A and 8B above. In this embodiment, however, a spring 340 is contained in a housing 342 and used such that it imparts force on the piston 64 in the fluid delivery cartridge 40. The spring itself imparts the force along the axis that the piston 64 moves. This is a simpler mechanism than that of FIGS. 8A and 8B but may lengthen the overall fluid delivery assembly. Again, as the fluid is withdrawn from the cartridge 40 shown in FIG. 9, the compressed spring 340 will expand and provide an assistive force against the piston 64 within the cartridge 40.

Figure 10:
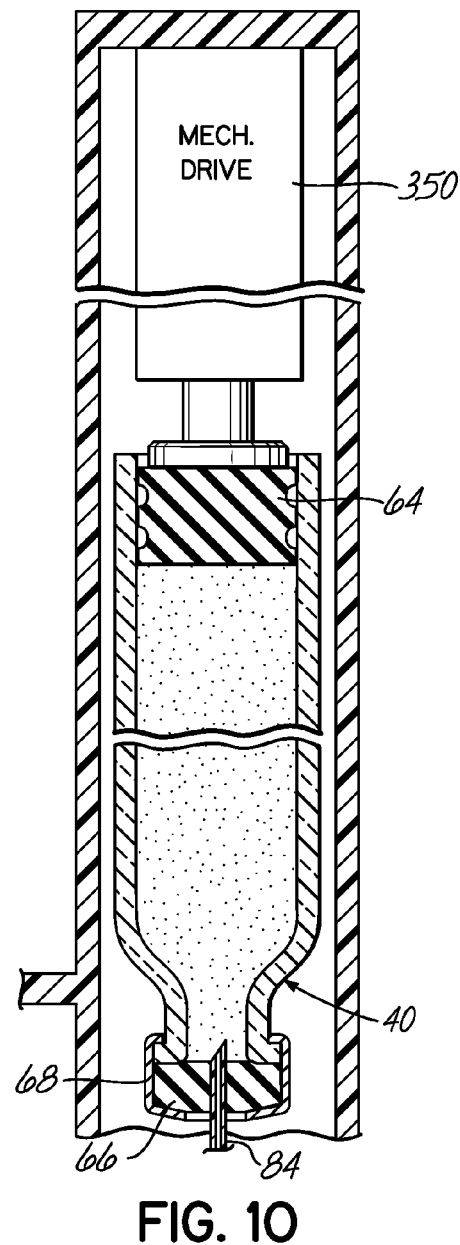
FIG. 10 is a cross sectional view of another alternative fluid delivery assembly utilizing a mechanical drive, such as a screw drive mechanism, for forcing liquid out from the cartridge.

FIG. 10 illustrates a system having a suitable mechanical drive mechanism 350 for forcing fluid from the cartridge to effect dosing (i.e., medication filling) of a needle-free injector (not shown) by using the dosing mechanism capability of the mechanism 350 and pushing the piston 64 of the cartridge 40 equivalent to a desired dose amount to be transferred into the needle-free syringe 94. For example, this may be similar to an inline screw drive system used in a pen style needle injector of Eli Lilly and Company, Indianapolis, Ind. that is sold under the Luxura™ brand name. This may provide a mechanical advantage of, for example, 4:1 for supplying all of the force necessary to depress the piston 64 into the cartridge 40 and transfer the necessary dose of fluid from the cartridge 40 into a suitable needle free injector (not shown).

Figure 11:
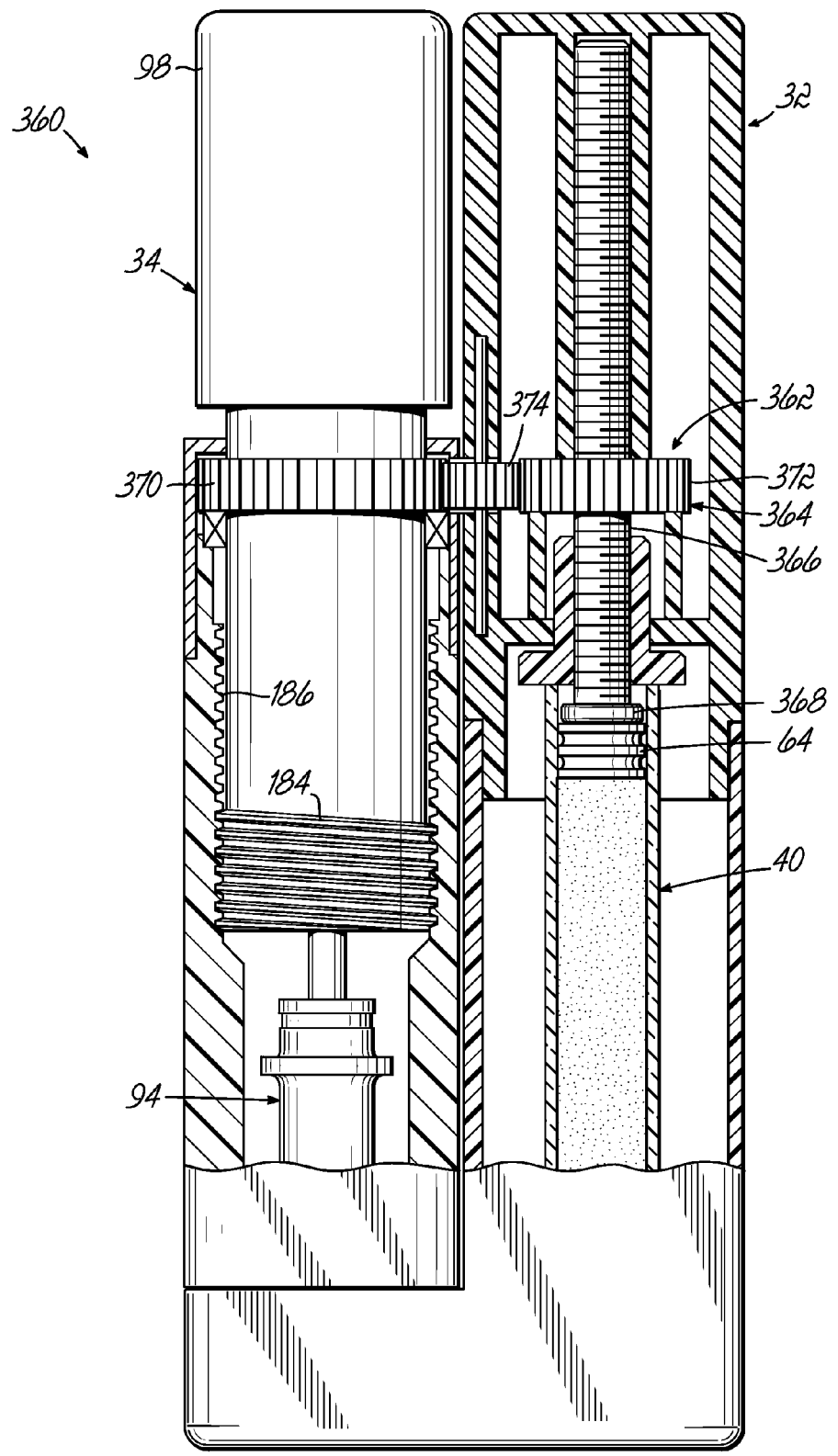
FIG. 11 is a schematic, partial cross sectional view of another alternative side-by-side needle free fluid injection device utilizing a lateral integrated gear transmission system to assist with piston movement simultaneously with vacuum induced transfer of fluid.

FIG. 11 schematically illustrates another example of a side-by-side needle free injection device 360 having an alternative mechanical assist device 362 for assisting the delivery of fluid from the cartridge 40 during a dosing procedure. Other details of the device 360 have been eliminated from FIG. 11 for clarity. Generally, this assist device 362 includes a gear system 364 coupled with an externally threaded leadscrew drive 366 bearing on the piston 64 within the fluid delivery cartridge 40. A freely rotatable wheel or hub 368 is coupled to the end of the externally threaded leadscrew drive 366 to accommodate the rotation of the externally threaded leadscrew drive 366 relative to the non-rotating piston 64.

Generally, as the dosing knob or sleeve 98 of the injector 34 is rotated to withdraw the plunger (not shown) via a threaded element 184, the gear system 364 converts this rotation into rotation of the externally threaded leadscrew drive 366 which then simultaneously rotates and translates or moves downward against the piston 64 to provide an assistive force to the piston 64 during downward movement thereof into the cartridge 40 as fluid is being withdrawn into the injector side of the device 360. The gear system 364 more specifically may include a first gear 370 that rotates with the dosing knob 98 and second gear 372 that rotates around the externally threaded leadscrew drive 366. The second gear 372 includes mating internal threads (not shown) engaged with the external threads of the rod 366. An intermediate and rotatably mounted slave gear 374 engages with the first and second gears 370, 372 to transfer rotation of the first gear 370 to the second gear 372. Thus, as the dosing knob 98 is rotated to withdraw the plunger (not shown) generally as previously described, this withdraws fluid from the cartridge 40 and simultaneously rotates the externally threaded leadscrew drive 366 such that it travels downwardly providing an assistive force against the piston 64 within the cartridge 40.

Figure 12A:
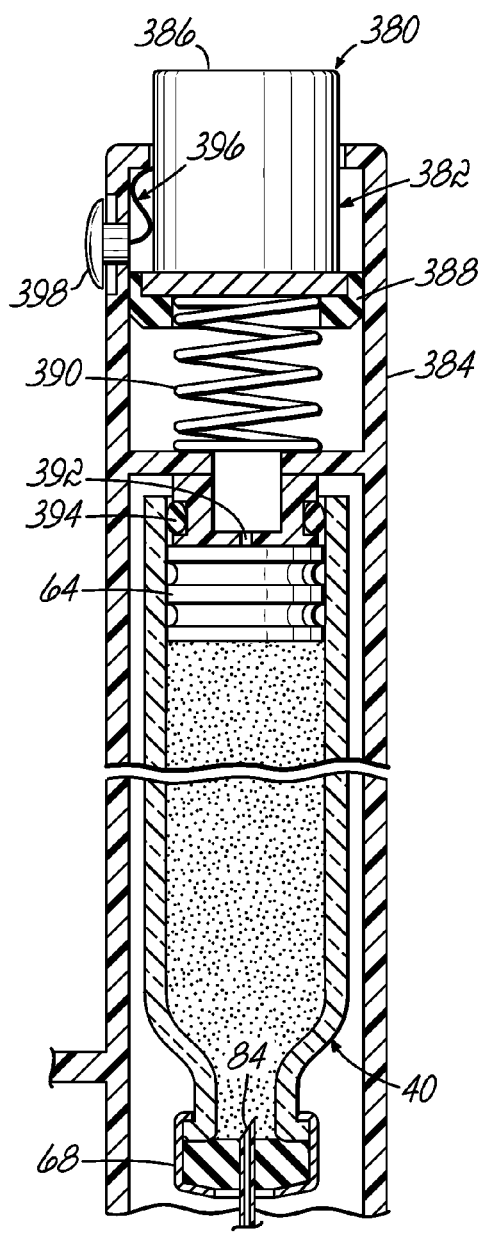
FIG. 12A is a schematic, cross sectional view of another alternative fluid delivery assembly utilizing an air pump for providing an assistive force against the piston in the fluid delivery cartridge.
Figure 12B:
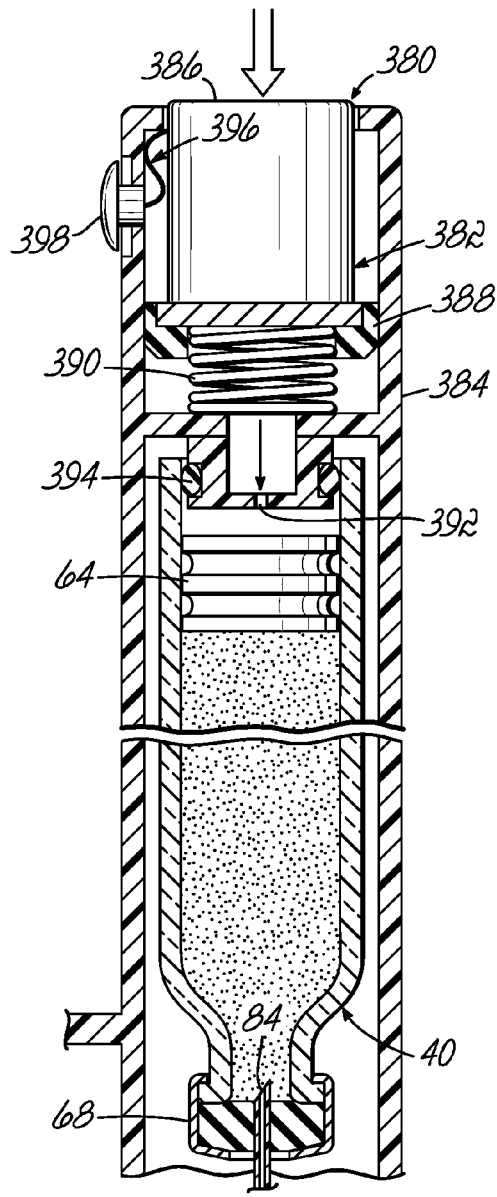
FIG. 12B is a cross sectional view of the fluid delivery assembly shown in FIG. 12A, but illustrating actuation of the air pump.

FIGS. 12A and 12B illustrate respective non-actuated and actuated conditions of another alternative assist mechanism 380 for providing an assistive force against the piston 64 of a fluid delivery cartridge 40. In particular, assist device 380 provides pressurized air against an upper side of the piston 64. Assist device 380 includes a push button mechanism 382 that slides within a chamber of a suitable housing 384. The push button mechanism 382 more specifically comprises a push button 386 coupled with a sliding seal assembly 388 and movable against a compression spring 390 within the housing 384. When the push button 386 is depressed as shown in FIG. 12B, this provides a compressive force against the spring 390 and compresses the air within the housing 384. The interior chamber of the housing 384 communicates with the interior of the cartridge 40 through an aperture 392 contained in a seal assembly 394. A latch 396, schematically shown in FIGS. 12A and 12B, may be used to retain the push button 386 in the downward or actuated position shown in FIG. 12B. A latch button 398 may be depressed to release the push button 386 and reset the air pressurization mechanism 380. It will be appreciated that the air pressure developed by depressing the push button 386 will provide a force against the upper side of the piston 64 thereby providing an assistive force to the downward movement of the piston 64 as fluid is withdrawn from the cartridge 40 through the piercing member 84. The mechanism 380 can allow a repeated number of air compressions to increase the force against piston 64 in cases where excessive friction may exist between piston 64 and cartridge body 58.

While the present invention has been illustrated by a description of a preferred embodiment and while this embodiment has been described in some detail, it is not the intention of the Applicants to restrict or in any way limit the scope of the appended claims to such detail. Additional advantages and modifications will readily appear to those skilled in the art. The various features of the invention may be used alone or in numerous combinations depending on the needs and preferences of the user. This has been a description of the present invention, along with the preferred methods of practicing the present invention as currently known. However, the invention itself should only be defined by the appended claims.

What is claimed is:

1. A device for injecting a fluid dose into a body of a patient comprising:
  a needle-free injecting assembly constructed and arranged to deliver the fluid dose into the body, the needle-free injecting assembly including:
    a needle-free syringe defining an injection chamber configured to receive the fluid dose, and an outlet; and
    a plunger movable within the injection chamber, the plunger configured to be drawn away from the outlet to apply a vacuum force within the injection chamber;
  a fluid delivery assembly configured to deliver the fluid dose to the needle-free injecting assembly, the fluid delivery assembly including:
    a housing defining an interior space therein;
    a cartridge defining a reservoir for containing the fluid, the cartridge constructed and arranged to be received by the interior space, the cartridge having a first end and a second end defining an outlet;
    a movable piston contained within the first end of the cartridge;
    a drive train for applying a force to the movable piston; and
    a sensing assembly constructed and arranged to control at least the drive train; and
  an adapter removably coupled to the needle-free injecting assembly and fluidly coupling the cartridge to the needle-free injecting assembly, the adapter having a fluid flow passage extending transverse to an axis extending along a length of the needle-free injecting assembly,
  wherein the sensing assembly directs the drive train to apply a force to the movable piston for overcoming adhesion or static friction between the movable piston and the cartridge while the vacuum force draws the fluid dose from the cartridge through the adapter and into the injection chamber of the needle-free injecting assembly.

2. The device of claim 1, further comprising:
  a magnet coupling the needle-free injecting assembly to the fluid delivery assembly.

3. The device of claim 2, wherein:
  the magnet additionally provides feedback to the sensing assembly concerning whether the needle-free injecting assembly is coupled to the fluid delivery assembly.

4. The device of claim 1, further comprising:
  a mechanical latch coupling the needle-free injecting assembly to the fluid delivery assembly.

5. The device of claim 1, wherein:
  the sensing assembly causes the drive train to move in an opposite direction when the sensing assembly receives input concerning the operation of the needle-free injecting assembly.

6. The device of claim 5, wherein:
  said input relates to an output from a sensor concerning the amount of force applied to the drive train.

7. The device of claim 5, wherein:
  said input relates to an output from a sensor related to the fluid pressure during delivery from the needle-free injecting assembly to the cartridge.

8. The device of claim 1, wherein:
  the sensing assembly indicates when a fluid dose below a predetermined amount remains in the cartridge.

9. The device of claim 8, wherein:
  the indicating is performed by activating a visual indicator.

10. The device of claim 8, wherein:
  the indicating is performed by activating an acoustical indicator.

11. The device of claim 1, wherein:
the drive train assists in transferring the fluid from both the cartridge to the needle-free injecting assembly and from the needle-free injecting assembly to the cartridge.

12. The device of claim 1, wherein:
the sensing assembly indicates when the needle-free injecting assembly is being coupled to the fluid delivery assembly.

13. The device of claim 1, wherein:
the sensing assembly indicates when the needle-free injecting assembly is being removed from the fluid delivery assembly.

14. The device of claim 13, wherein:
the drive train lessens the pressure in the cartridge in response to the indication of the sensing assembly that the needle-free injecting assembly is being removed.

15. The device of claim 1, wherein the outlet of the needle-free injecting assembly is adapted to allow discharge of the fluid dose during needle-free injection into the body of the patient, and wherein the plunger of the needle-free injecting assembly is adapted to force the fluid dose from the injection chamber through the outlet.

16. The device of claim 1, wherein the sensing assembly further comprises:
a sensor to produce an output related to the amount of the fluid dose transferred into the needle-free injecting assembly.

17. The device of claim 1, wherein:
the fluid delivery assembly positioned in a side-by-side arrangement with the needle-free injecting assembly.

18. The device of claim 1, wherein the fluid flow passage further comprises:
a first fluid passage fluidly coupled to the cartridge;
a second fluid passage adapted to be fluidly coupled to the needle-free injecting assembly; and
a third fluid passage in fluid communication between the first fluid passage and the second fluid passage, the third fluid passage extending transverse to the first and second fluid passages.

19. The device of claim 18, further comprising a piercing member containing said first fluid passage, wherein:
the second end of the cartridge being closed off using a seal;
wherein fluidly coupling said adapter to said cartridge occurs by puncturing the seal with the piercing member.

20. The device of claim 1, wherein:
the cartridge is coupled in a removable manner to said adapter.

21. A device for injecting a fluid dose into a body of a patient comprising:
a needle-free injecting assembly constructed and arranged to deliver the fluid dose into the body, the injecting assembly including:
a needle-free syringe defining an injection chamber configured to receive the fluid dose, and an outlet, and
a plunger movable within the injection chamber, the plunger configured to be drawn away from the outlet to apply a vacuum force within the injection chamber; and
a fluid delivery assembly configured to deliver the fluid dose to the injecting assembly, the fluid delivery assembly including:
a cartridge defining a reservoir for containing the fluid dose, the cartridge having a first end and a second end defining an outlet,
a movable piston contained within the first end of the cartridge,
an adapter removably coupled to the injecting assembly and fluidly coupling the cartridge to the injecting assembly, and
a powered drive train for applying a force to the movable piston for facilitating aspiration of the fluid from the cartridge while the vacuum force draws the fluid dose from the cartridge through the adapter and into the injection chamber of the injecting assembly.

22. The device of claim 21, further comprising a sensing assembly constructed and arranged to sense the force applied to the movable piston and the cartridge and to control at least the drive train to direct the drive train to apply the force to the movable piston for overcoming adhesion or static friction between the cartridge and the movable piston during delivery of the fluid from the cartridge to the injecting assembly.

23. The device of claim 21, wherein the adapter has a fluid flow passage extending transverse to an axis extending along a length the injecting assembly and is configured for positioning the fluid delivery assembly in a side-by-side arrangement with the needle-free injecting assembly.

24. A device for injecting a fluid dose into a body of a patient comprising:
a needle-free injecting assembly constructed and arranged to deliver the fluid dose into the body, the injecting assembly including:
a needle-free syringe defining an injection chamber configured to receive the fluid dose, and an outlet, and
a plunger movable within the injection chamber, the plunger configured to be drawn away from the outlet to apply a vacuum force within the injection chamber; and
a fluid delivery assembly configured to deliver the fluid dose to the injecting assembly, the fluid delivery assembly including:
a cartridge defining a reservoir for containing the fluid, the cartridge having a first end and a second end defining an outlet,
a movable piston contained within the first end of the cartridge,
an adapter removably coupled to the injecting assembly and fluidly coupling the cartridge to the injecting assembly,
a powered drive train for applying a force to the movable piston, and a sensing assembly constructed and arranged to sense the force applied to the movable piston and the cartridge and to control at least the drive train to direct the drive train to apply the force to the movable piston for overcoming adhesion or static friction between the cartridge and the movable piston while the vacuum force draws the fluid dose from the cartridge through the adapter and into the injection chamber of the injecting assembly.

* * * * *